(12) United States Patent
Lohrman et al.

(10) Patent No.: US 11,021,447 B2
(45) Date of Patent: Jun. 1, 2021

(54) FLUORESCENT HALOGEN BONDING ARYLETHYNYL SCAFFOLDS FOR ANION RECOGNITION

(71) Applicants: University of Oregon, Eugene, OR (US); University of Montana, Missoula, MT (US)

(72) Inventors: Jessica Lohrman, Eugene, OR (US); Darren W. Johnson, Eugene, OR (US); Michael M. Haley, Eugene, OR (US); Orion B. Berryman, Missoula, MT (US); Asia M. Riel, Missoula, MT (US); Daniel A. Decato, Missoula, MT (US)

(73) Assignees: University of Oregon, Eugene, OR (US); University of Montana, Missoula, MT (US)

( * ) Notice: Subject to any disclaimer, the term of this patent is extended or adjusted under 35 U.S.C. 154(b) by 0 days.

(21) Appl. No.: 16/401,037

(22) Filed: May 1, 2019

(65) Prior Publication Data

US 2019/0345113 A1 Nov. 14, 2019

Related U.S. Application Data

(60) Provisional application No. 62/671,280, filed on May 14, 2018.

(51) Int. Cl.
*C07D 233/56* (2006.01)
*C07D 213/22* (2006.01)
(Continued)

(52) U.S. Cl.
CPC ......... *C07D 233/56* (2013.01); *C07D 213/22* (2013.01); *C07D 213/90* (2013.01); *G01N 21/6428* (2013.01)

(58) Field of Classification Search
CPC .............................. C07D 233/56; C07D 213/22
(Continued)

(56) References Cited

U.S. PATENT DOCUMENTS 7,265,378 B2 * 9/2007 Lecloux ................ C07C 211/49
257/40
7,803,946 B2 9/2010 Haley et al.
(Continued)

FOREIGN PATENT DOCUMENTS

CN 1810801 * 2/2006

OTHER PUBLICATIONS

Pearson et al., Journal of organic chemistry (1997), 62(5), 1376-1387.*

(Continued)

Primary Examiner — Niloofar Rahmani
(74) Attorney, Agent, or Firm — Klarquist Sparkman, LLP

(57) ABSTRACT

A compound, or a protonate or salt thereof, of formula I:

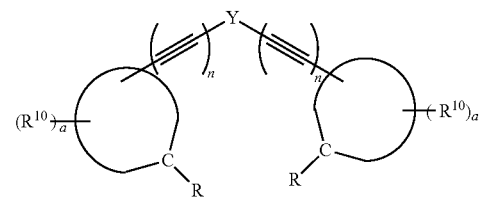

Formula I wherein Y is aryl, substituted aryl, heteroaryl, or substituted heteroaryl;

n is 1 or 2;

each $R^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;

a is 0 to 4;

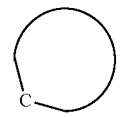

is an aryl or heteroaryl ring; and each R is independently halogen, carbonylamino, sulfonamide, carboxylic acid or hydrogen, provided at least one R is a halogen; and provided that if Y is are not

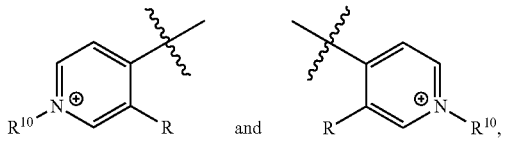

respectively.

27 Claims, 14 Drawing Sheets

(51) Int. Cl.
  *G01N 21/64* (2006.01)
  *C07D 213/90* (2006.01)
(58) Field of Classification Search
  USPC .................................................. 546/352
  See application file for complete search history.

(56) References Cited

U.S. PATENT DOCUMENTS

| | | | |
|---|---|---|---|
| 8,841,460 | B2 | 9/2014 | Johnson et al. |
| 9,664,696 | B1 | 5/2017 | Pluth et al. |
| 9,964,531 | B2 | 5/2018 | Haley et al. |
| 2007/0202198 | A1 | 8/2007 | Purcell |
| 2008/0167472 | A1 | 7/2008 | Haley et al. |
| 2009/0184005 | A1 | 7/2009 | Zhang et al. |
| 2010/0099683 | A1 | 4/2010 | Tomkinson et al. |
| 2015/0355153 | A1 | 12/2015 | Haley et al. |
| 2017/0350870 | A1 | 12/2017 | Haley et al. |
| 2018/0258347 | A1* | 9/2018 | Mori ............ C07D 403/10 |

OTHER PUBLICATIONS

Sun et al., Organometallics (2001), 20(11), 2353-2358.*
Zhao et al., New journal of chemistry (2004), 28(8), 912-918.*
Wu et al., Journal of Photochemistry and photobiology, b: Biology (2007), 88(2-3), 180-184.*
Ullah et al., Synlett (2009), (5), 838-842.*
Ramirez et al., ARKIVOC (2011), (3), 140-155.*
Hirano et al., Journal of organic Chemistry (2011), 76(21), 9068-9080.*
Maarten et al., Journal of medicinal chemistry (2013), 56(7), 2828-2840.*
Landarani et al., European Journal of organic chemistry, (2014), 2014(25), 5603-5609.*
Yu et al., Journal of Medicinal Chemistry (2015), 58(15), 5916-5929.*
Reimann et al., Organic & Biomolecular Chemistry (2017), 15(6), 1510-1520.*
Bailey et al., "Chemiluminescent Detection of Enzymatically Produced Hydrogen Sulfide: Substrate Hydrogen Bonding Influences Selectivity for $H_2S$ over Biological Thiols," *J. Am. Chem. Soc.*, vol. 135, pp. 16697-16704, 2013.
Berryman et al., "Water and hydrogen halides serve the same structural role in a series of 2+2 hydrogen-bonded dimers based on 2,6-bis(2-anilinoethynyl)pyridine sulfonamide receptors," *Angewandte Chemie* 47(1):117-120, 2008.
Brown et al., "Halogen bonding anion recognition," *Chem. Commun.*, 56(52): 8645-8658, Jun. 6, 2016.
Butler et al., "Bipyridylacetylenes 1: the synthesis of some bipyridylacetylenes via the palladium-catalyzed coupling of acetylenes with 2,2'-dibromobipyridyl, and the single crystal X-ray structure of 6,6'-bisphenylethynyl-2,2'-bipyridine," *Can. J. Chem.* 69:1117-1123, 1991.

Carroll et al., "Anion-dependent fluorescence in bis(anilinoethynyl)pyridine derivatives: switchable On-Off and Off-On responses," *Chemical Communications* 47:5539-5541, 2011.
Carroll et al., "Protonation activates anion binding and alters binding selectivity in new inherently fluorescent 2,6-bis(2-anilinoethynyl)pyridine bisureas," *Chemical Communications* 2520-2522, 2009 (Available online Mar. 27, 2009).
Dash et al., "Diarylethynyl amides that recognize the parallel conformation of genomic promoter DNA G-quadruplexes," *Journal of the American Chemical Society* 130(47):15950-15956, 2008 (published online Nov. 4, 2008).
Dash et al., "G-quadruplex recognition by bis-indole carboxamides," *Chemical Communications* 26:3055-3057, 2008.
Droz et al., "Synthesis of highly-functionalized, optically active disaccharide receptors by sequential aryl-alkyne cross-and oxidative acetylenic homo-coupling," *J. Chem. Soc.* 4224-4226, 2000.
Engle et al., "Synthesis and Optoelectronic Properties of 2,6-Bis(2-anilino-ethynyl)pyridine Scaffolds," *Chem. Sci.* 3:1105-1110, 2012.
Ferrara et al., "Synthesis and Characterization of a Copper(1) Triflate Complex of 1,2:5,6:9,10-Tribenzocyclododeca-1,5,9-triene-3,7,11-triyne," *Organometallics* 6:676-678, 1987.
Ferrara et al., "Synthesis and Characterization of the First Transition-Metal Complex of 1,2:5,6:9,10-Tribenzocyclododeca-1,5,9-triene-3,7,11-triyne," *J. Am. Chem. Soc.* 107:6719-6721, 1985.
Gerhardt et al., "Controlling polymer properties through dynamic metal-ligand interactions: supramolecular cruciform made easy," *Chem. Eur. J.* 13(16):4467-4474, 2007.
Gerhardt et al., "Supramolecular cruciforms," *Chemical Communications* 20:2141-2143, 2006.
Gu et al., "Development of a boron-dipyrromethene-$Cu^{2+}$ ensemble based colorimetric probe toward hydrogen sulfide in aqueous media," *Tetrahedron Letters* 52:5000-5003, 2011.
Hartle et al., "A Synthetic Supramolecular Receptor for the Hydrosulfide Anion," *Angewandte Chemie International Edition*, 55(38): 11480-11484, Aug. 11, 2016. (Abstract only).
Hauck et al., "Phenothiazine Cruciforms: Synthesis and Metallochromic Properties," *Journal of Organic Chemistry* 72(18):6714-6725, 2007.
Jarosz et al., "Microplate-Based Colorimetric Detection of Free Hydrogen Sulfide," *Analytical Chemistry* 85:3638-3643, 2013.
Jia et al., "Novel Phosphorescent Cyclometalated Organotin(IV) and Organolead(IV) Complexes of 2,6-Bis(2'-indolyl)pyridine and 2,6-Bix[2'-(7-azaindolyl)]pyridine," *Organometallics* 22:4070-4078, 2003.
Johnson et al., "Aryl-Acetylene Scaffolding as Receptors in Supramolecular Chemistry," presentation through Department of Chemistry & Materials Science Institute of the University of Oregon, 26 pages, 2007.
Johnson et al., "Synthesis and characterization of pyridine- and thiophene-based platinacyclynes," *Journal of Organometallic Chemistry* 691:413-421, 2006 (available online Oct. 25, 2005).
Lee et al., "Detection of hydrogen peroxide with chemiluminescent micelles," *International Journal of Nanomedicine* 3(4):471-476, 2008.
Leininger et al., "Self-Assembly of Discrete Cyclic Nanostructures Mediated by Transition Metals," *Chem. Rev.* 100:853-908, 2000.
Lippert et al., "Reaction-Based Fluorescent Probes for Selective Imaging of Hydrogen Sulfide in Living Cells," *Journal of the American Chemical Society* 133:10078-10080, 2011.
Liu et al., "A visible light excitable colorimetric and fluorescent ESIPT probe for rapid and selective detection of hydrogen sulfide," *Organic & Biomolecular Chemistry* 12:438-445, 2013.
Liu et al., "Capture and Visualization of Hydrogen Sulfide by a Fluorescent Probe," *Angew. Chem. Int. Ed.* 50:10327-10329, 2011.
Maity et al., "A probe for ratiometric near-infrared fluorescence and colorimetric hydrogen sulfide detection and imaging in living cells," *RSC Advances* 4:11147-11151, 2014.
Massena et al., "Solution and solid-phase halogen and C—H hydrogen bonding to perrhenate," *Chem. Commun.*, 8(51): 1417-1420, 2015.
McGrier et al., "Hydroxy-cruciforms," *Chemical Communications* 21:2127-2129, 2007.

(56) References Cited

OTHER PUBLICATIONS

Montoya et al., "Selective turn-on fluorescent probes for imaging hydrogen sulfide in living cells," *Chemical Communications* 48:4767-4769, 2012.
Montoya et al., "Development of Selective Colorimetric Probes for Hydrogen Sulfide Based on Nucleophilic Aromatic Substitution," *J. Org. Chem.*, vol. 78, pp. 6550-6557, 2013.
Peng et al., "A Fluorescent Probe for Fast and Quantitative Detection of Hydrogen Sulfide in Blood," *Angew. Chem. Int. Ed.* 50:9672-9675, 2011.
Pucher et al., "Structure-Activity Relationship in D-π-A-π-D-Based Photoinitiators for the Two-Photon-Induced Photopolymerization Process," *Macromolecules* 10 pages, 2009.
Qian et al., "Selective fluorescent probes for live-cell monitoring of sulphide," *Nature Communications* 2(495)1-7, 2011.
Riel et al., "Experimental investigation of halogen-bond hard-soft acid-base complementarity," *Acta Cryst. Sec. B. Struc. Sci. Cryst. Eng. Mater.*, 73(2): 203-209, Apr. 2017.
Riel et al., "The intramolecular hydrogen bonded-halogen bond: a new strategy for preorganization and enhanced binding," *Chemical Science*, 9(26): 5828-5836, Jun. 21, 2018.
Roda et al., "Analytical chemiluminescence and bioluminescence: latest achievements and new horizons," *Anal Bioanal Chem* 402:69-76, 2011.
Saha et al., "A colorimetric and fluorometric BODIPY probe for rapid, selective selection of $H_2S$ and its application in live cell imaging," *Organic & Biomolecular Chemistry* 11:8166-8170, 2013.
Sasakura et al., "Development of a Highly Selective Fluorescence Probe for Hydrogen Sulfide," *Journal of the American Chemical Society* 133:18003-18005, 2011.
Shen et al., "Measurement of plasma hydrogen sulfide in vivo and in vitro," *Free Radical Biology & Medicine* 50:1021-1031, 2011.
Sun et al., "Solvatochromism and fluorescence response of a halogen bonding anion receptor," *New J. Chem.*, 42(13): 10489-10492, Jul. 7, 2018.

Van de Bittner et al., "In vivo imaging of hydrogen peroxide production in a murine tumor model with a chemoselective bioluminescent reporter," *PNAS* 107(50):21316-21321, 2010.
Walters et al., "Experimental Studies of Light-Induced Charge Transfer and Charge Redistribution in (X2-Bipyridine)Re(CO)3Cl Complexes," *Inorganic Chemistry* 41:2909-2919, 2002.
Wei et al., "NBD-based colorimetric and fluorescent turn-on probes for hydrogen sulfide," *Organic & Biomolecular Chemistry* 12:479-485, 2013.
Wilson et al., "Switching of Intermolecular Charge Transfer in Cruciforms: Metal Ion Sensing," *Journal of the American Chemical Society* 172(12):4124-4125, 2005.
Wu et al., "A selective colorimetric and ratiometric fluorescent probe for hydrogen sulfide," *Organic & Biomolecular Chemistry* 10:8342-8347, 2012.
Yamaguchi et al., "Evaluation of chemiluminescence reagents for selective detection of reactive oxygen species," *Analytica Chimica Acta* 665:74-78, 2010.
Zhang et al., "A dicopper complex chemiluminescence probe for the determination of thiols in the extracts of murine P388 lymphocytic leukemia cell," *Chem. Commun.* pp. 5624-5626, 2009.
Zhang et al., "Highly selective and sensitive colorimetric probe for hydrogen sulfide by a copper (II) complex of azo-dye based on chemosensing ensemble approach," *Spectrochimica Acta Part A: Molecular and Biomolecular Spectroscopy* 90:35-39, 2012.
Zhang et al., "On-Site Visual Detection of Hydrogen Sulfide in Air Based on Enhancing the Stability of Gold Nanoparticles," *ACS Applied Materials & Interfaces* 6:6300-6307, 2014.
Zhao et al., "A highly selective colorimetric chemodosimeter for fast and quantitative detection of hydrogen sulfide," *Analyst* 137:5576-5580, 2012.
Zucchero et al., "Cruciforms as Functional Fluorophores: Response to Protons and Selected Metal Ions," *J. Am. Chem. Soc.*, vol. 128, pp. 11872-11881, 2006.

\* cited by examiner

Huber[29]
Sterics

Molina[80]
π-π Stacking

Schubert[61]
External Hydrogen Bonding

Berryman
Hydrogen Bonded-Halogen Bond
This Work

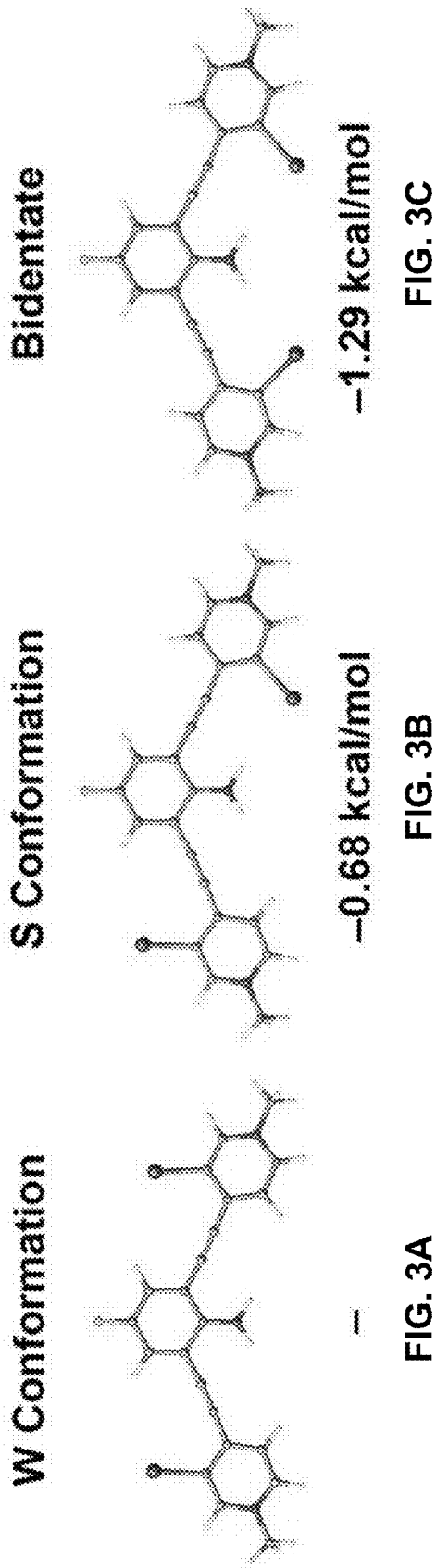

FLUORESCENT HALOGEN BONDING ARYLETHYNYL SCAFFOLDS FOR ANION RECOGNITION

CROSS-REFERENCE TO RELATED APPLICATION

This application claims the benefit of U.S. Provisional Application No. 62/671,280 filed on May 14, 2018, the entirety of which is incorporated herein by reference.

ACKNOWLEDGMENT OF GOVERNMENT SUPPORT

This invention was made with government support under CAREER CHE-1555324 awarded by the National Science Foundation and under R01GM087398 awarded by the National Institutes of Health. The government has certain rights in the invention.

BACKGROUND

The synthesis of new molecules designed to bind or sense and report the presence of a particular substrate is an area of chemistry that is attracting attention. There exists a general lack of ligand-specific host molecules, such as specific hosts for toxic ions and small molecules of interest. There also is a dearth of specific hosts that report binding events, for example by exhibiting a spectral shift upon binding, such as an altered fluorescent response. In fact, structures of fluorescent coordination complexes are generally poorly understood, which makes the rational design of functional hosts and sensors a challenging undertaking.

Interest in supramolecular sensors for the detection of analytes has received considerable attention over the past two decades. Such systems exploit non-covalent interactions between a guest molecule and a host molecule to induce a change in the host (e.g. NMR shift, color, fluorescence, electrochemical behavior etc.). These systems are advantageous when compared to chemodosimeters because these non-covalent interactions are reversible, which allows one to monitor an analyte dynamically. Arguably the most powerful of these sensors exploit a fluorescence/colorimetric change due to their inherent sensitivity.

The detection of ionic species, in particular the selective detection of a particular ionic species in the presence of another is difficult. The detection of anionic species is a particular challenge, as anions are difficult to bind and are generally larger than cations leading to a smaller charge-to-radius ratio.

In addition, preorganization is a central tenet of supramolecular chemistry that facilitates precise molecular function and higher order self-assembly. Preorganized biomolecular structures rely on noncovalent interactions for their critical role in natural processes (e.g. catalysis, ion channels, signaling, nutrient transport, and antibodies).

SUMMARY

Disclosed herein are compounds, or a protonate or salt thereof, of formula I:

Formula I

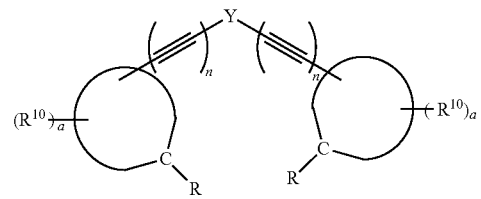

wherein Y is aryl, substituted aryl, heteroaryl, or substituted heteroaryl;
n is 1 or 2;
each $R^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;
a is 0 to 4;

is an aryl or heteroaryl ring; and
each R is independently halogen, carbonylamino, sulfonamide, carboxylic acid or hydrogen, provided at least one R is a halogen; and
provided that if Y is then

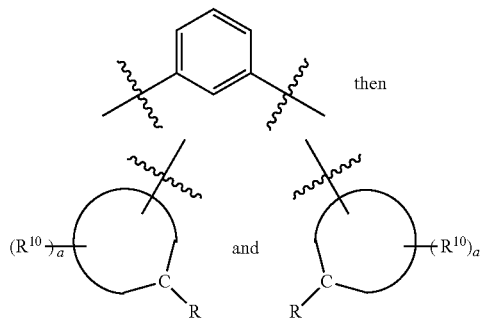

are not

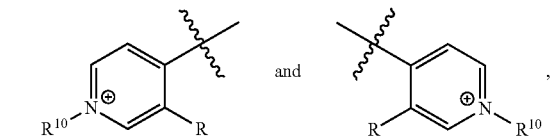

respectively.

Also disclosed herein is a compound, or a protonate or salt thereof, of formula II:

Formula II

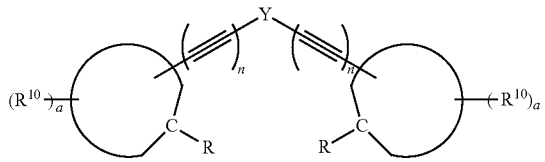

wherein Y is

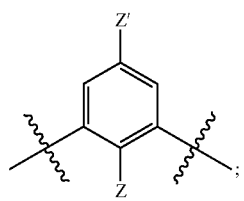

wherein Z is hydrogen, halogen, amino, substituted amino, hydroxy, amido, urea or sulfonamido; Z' is hydrogen, halogen, substituted alkyl (e.g., haloalkyl such as —CF$_3$), nitro, or cyano, provided Z and Z' are not both hydrogen; n is 1 or 2;

each R$^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;

a is 0 to 4;

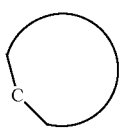

is an aryl or heteroaryl ring; and each R is independently halogen, carbonylamino, sulfonamide, carboxylic acid or hydrogen;

and the

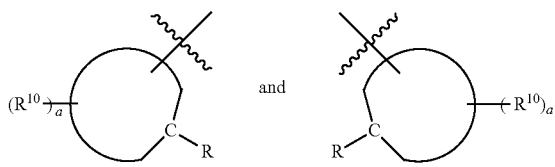

portions of the compound of formula II are

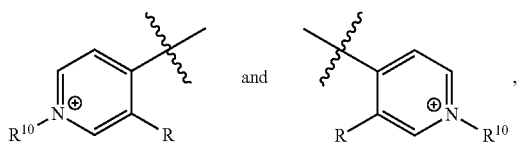

respectively.

Further disclosed herein is a receptor-ligand structure comprising any of the receptor compounds disclosed herein and a ligand. In certain embodiments, the ligand includes at least one anion selected from Cl$^-$, Br$^-$, I$^-$, H$_2$PO$_4^-$, HSO$_4^-$, ClO$_4^-$, NO$_3^-$, PF$_6^-$, TsO$^-$, OTf$^-$, BAr$^{F-}$, BF$_4^-$, HS$^-$, SbF$_6^-$, ReO$_4^-$, TcO$_4^-$ or SCN$^-$.

Further disclosed herein is a method for detecting for the presence of a target of interest in a system, comprising contacting a compound as disclosed herein with a sample from the system.

Exemplary compounds exhibit shifts in their spectral properties upon ligand binding. Accordingly, also disclosed are methods for using the host compounds to detect targets of interest, including neutral, cationic and anionic targets.

The foregoing will become more apparent from the following detailed description, which proceeds with reference to the accompanying figures.

BRIEF DESCRIPTION OF THE DRAWINGS

FIGS. 3A-C are gas-phase DFT single point energy calculations of the three planar conformations of G2XBme$^{2+}$ highlight intramolecular HB-XB stabilization. Ball and stick models were produced from lowest energy conformations.

and 2b (d) in various solvents (for excitation wavelengths and details see SI). All spectra were recorded at 20 μM of receptor

DETAILED DESCRIPTION

Terminology

Figure 1A:
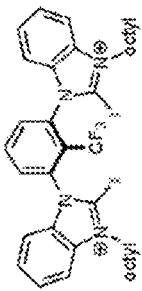
FIGS. 1A-1D show representative noncovalent preorganization strategies for XB receptors.
Figure 1B:
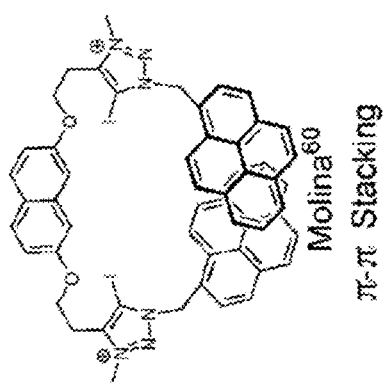
Figure 1C:
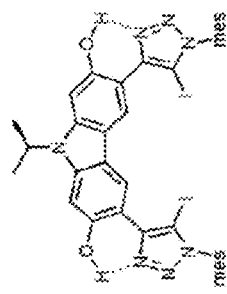

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R' can be, independently, hydrogen or an alkyl, alkenyl, alkynyl, acyl, aryl, aralkyl, cycloalkyl, halogenated alkyl, or heterocycloalkyl group. For example, an "alkylamino" or "alkylated amino" refers to —NRR', wherein at least one of R or R' is an alkyl. A suitable amine or amino group is acetamido.

The term "aminoalkyl" refers to alkyl groups as defined above where at least one hydrogen atom is replaced with an amino group (e.g., —$CH_2$—$NH_2$).

"Aminocarbonyl" alone or in combination, means an amino substituted carbonyl (carbamoyl), wherein the amino may optionally be mono- or di-substituted, such as, for example, with alkyl, aryl, acyl, aralkyl, cycloalkyl, cycloalkylalkyl, alkanoyl, alkoxycarbonyl, aralkoxycarbonyl and the like. For example, an aminocarbonyl may be represented by the formula —C(O)NRR', where R and R' independently can be, for example, a hydrogen, alkyl, alkenyl, alkynyl, acyl, aryl, aralkyl, cycloalkyl, halogenated alkyl, or heterocycloalkyl group.

The term "arylalkyl" refers to an alkyl group wherein an aryl group is substituted for a hydrogen of the alkyl group. An example of an arylalkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

A "carbonylamino" group may be —N(R)—C(O)—R (wherein each R is independently a substitution group such as, for example, alkyl, alkenyl, alkynyl, acyl, aryl, aralkyl, cycloalkyl, halogenated alkyl, amino, or heterocycloalkyl group, or H). A suitable carbonylamino group is acetamido.

The term "carboxylate" or "carboxyl" refers to the group —COO or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino Unless otherwise defined optionally substituted N-heterocycles includes pyridinium salts and the N-oxide form of suitable ring nitrogens. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$ alkyl)amino Unless otherwise defined optionally substituted N-heterocycles includes pyridinium salts and the N-oxide form of suitable ring nitrogens.

The term "polyether moiety" may be an oligomer (which is inclusive of dimers and higher repeating units) or a polymer. Illustrative polyether moieties include those derived from an aliphatic polyether (e.g., paraformaldehyde, polyethylene glycol (PEG), polypropylene glycol, and polytetramethylene glycol, and those derived from an aromatic polyether (e.g., polyphenyl ether or poly(p-phenylene oxide)). A preferred polyether moiety is derived from PEG, also referred to herein as a poly(ethylene oxide). The PEG may be a straight chain PEG or a branched PEG. PEG is also inclusive of methoxypolyethylene glycol. In certain embodiments, the number of repeating ethylene oxide units in the PEG moiety may range from 2 to 50, more particularly from 2 to 10. The polyether moiety may be covalently bonded to the core motif via PEGylation procedures.

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$acycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

"Sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $Cl_{1-3}$alkylsulfinyl groups are preferred, such as for example, —SOmethyl, —SOethyl and —SOpropyl.

The term "sulfonyl" refers to the group —$SO_2$H. The sulfonyl group can be further substituted with a variety of groups to form, for example, sulfonic acids, sulfonamides, sulfonate esters and sulfones.

The term "substituted sulfonyl" refers to a sulfonyl group having the hydrogen replaced with, for example a $C_{1-6}$alkyl group ("$C_{1-6}$alkylsulfonyl"), $C_{1-6}$haloalkyl group ("$C_{1-6}$haloalkylsulfonyl"), an aryl ("arylsulfonyl"), an aralkyl ("aralkylsulfonyl") and so on. Sulfonyl$C_{1-3}$alkyl groups are preferred, such as for example, —$SO_2$Me, —$SO_2$Et and —$SO_2$Pr.

The term "sulfonylamido" or "sulfonamide" refers to the group —$SO_2NH_2$.

Compounds, Compositions and Uses Thereof

Disclosed herein in certain embodiments are compounds utilizing neutral para-positioned electron withdrawing groups that are capable of polarizing halogen bond donating groups within an arylethynyl scaffold which is capable of anion recognition. The receptor compounds designed have been shown to reversibly bind anions in solution while demonstrating a spectroscopic response upon binding. These receptors may have a significant advantage in anion binding in competitive polar solvents. The compounds can provide solution-phase halogen-bond-mediated anion recognition processes for selectively detecting and/or extracting and/or transporting negatively charged species. Such species may play fundamental roles in a vast range of chemical, biological, medical and environmental processes. For example, these halogen bonding arylethynyl scaffolds pose an opportunity to sense anions in aqueous media which could directly be applied to agricultural and biomedical anion recognition. The compounds and methods disclosed herein address at least one of the intrinsic challenges associated with the design of selective host systems for negatively charged species: anions have low charge-to-radius ratios, high solvation enthalpies and poorly defined coordination preferences compared to cations; they are also pH sensitive and exhibit a wide range of geometries.

In further embodiments, disclosed herein are compounds utilizing intramolecular hydrogen bonded-halogen bond (HB-XB) as a novel method to preorganize halogen bonding (XBing) molecules, while generating a polarization-enhanced XB. The intramolecular HB-XB can be used to noncovalently preorganize a molecule while simultaneously enhancing the XB interaction in solution, solid, and in silico.

According to the unifying definition proposed by a recent IUPAC Task Group, a halogen bond (XB) "occurs when there is evidence of a net attractive interaction between an electrophilic region associated with a halogen atom in a molecular entity and a nucleophilic region in another, or the same, molecular entity."

In particular, disclosed herein are compounds, or a protonate or salt thereof, of formula I:

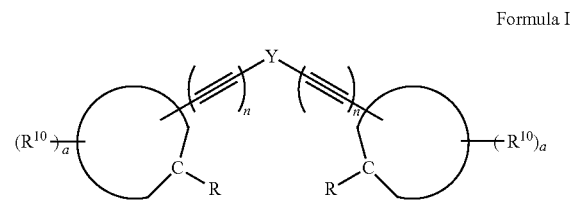

Formula I wherein Y is aryl, substituted aryl, heteroaryl, or substituted heteroaryl;

n is 1 or 2;

each $R^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;

a is 0 to 4;

is an aryl or heteroaryl ring; and each R is independently halogen, carbonylamino, sulfonamide, carboxylic acid or hydrogen, provided at least one R is a halogen; and provided that if Y is then and are not and respectively.

Also disclosed herein are compounds, or a protonate or salt thereof, of formula II:

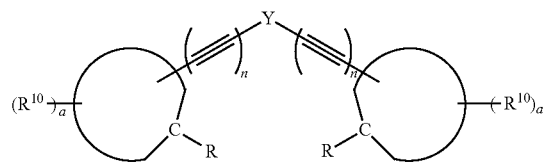

Formula II wherein Y is

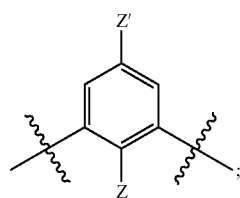

wherein Z is hydrogen, halogen, amino, substituted amino, hydroxy, amido, urea or sulfonamido; Z' is hydrogen, halogen, substituted alkyl (e.g., haloalkyl such as —$CF_3$), nitro, or cyano, provided Z and Z' are not both hydrogen;

n is 1 or 2;

each $R^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;

a is 0 to 4;

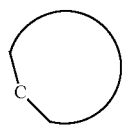

is an aryl or heteroaryl ring; and each R is independently halogen, carbonylamino, sulfonamide, carboxylic acid or hydrogen;

and the

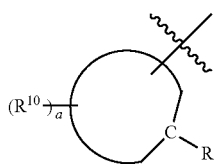 and 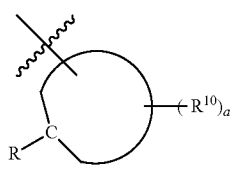

portions of the compound of formula II are

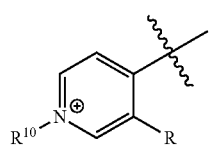 and 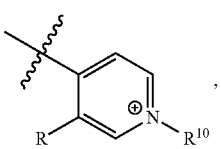, respectively.

Y can include any aromatic group such as phenylene or a heteroaromatic group. Illustrative Y groups include, without limitation, phenylene, pyridyl, bipyridyl, pyridinyl, pyrazinyl, pyrimidinyl, pyrrole, imidazole, triazole, thiophene, thiazole, furyl and oxazolyl groups. By way of example, such Y groups can be selected from

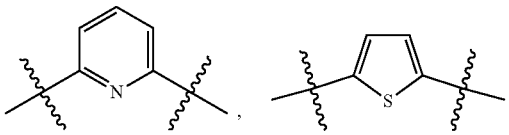

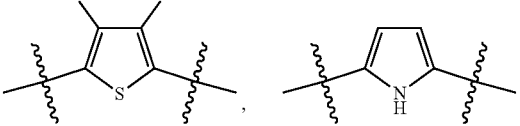

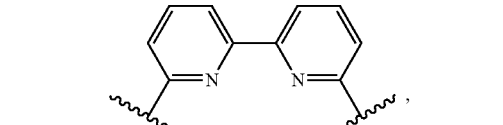

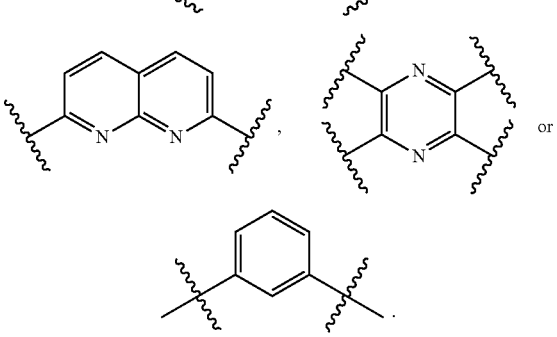 or

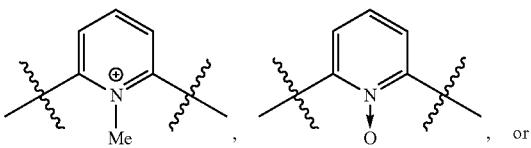

In certain embodiments, Y may be:

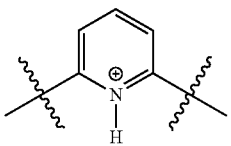

In certain embodiments, Y may be:

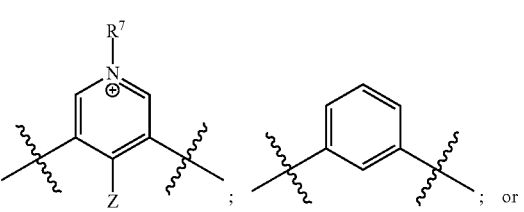

-continued

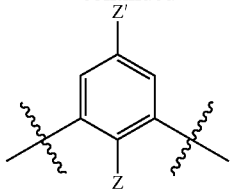

wherein Z is hydrogen, halogen, amino, substituted amino, hydroxy, amido, urea or sulfonamido; Z' is hydrogen, halogen, substituted alkyl (e.g., haloalkyl such as —CF$_3$), nitro, or cyano; and R$^7$ is hydrogen, alkyl, substituted alkyl, or polyethylene glycol.

In certain embodiments, R$^7$ is C$_1$-C$_6$ alkyl (particularly methyl), alkoxyalkyl, aminoalkyl, or sulfonylalkyl (particularly sulfonate alkyl anion such as —CH$_2$—CH$_2$—SO$_3$$^-$).

In certain embodiments, Z is —NH$_2$, —Br, or —I.
In certain embodiments, Z' is —F.
In certain embodiments, Z' is —F and Z is NH$_2$.
In certain embodiments, n is 1.
In certain embodiments, a is 1.
In certain embodiments,

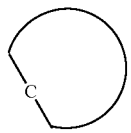

is a N-heterocyclic ring.

In certain embodiments,

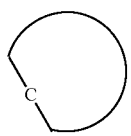

is a triazole.

In certain embodiments the

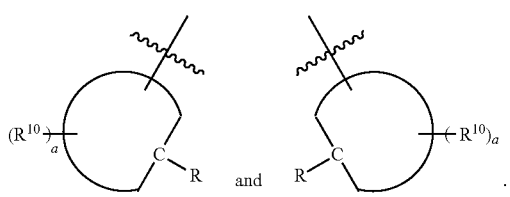

portions of the compound of formula I may be:

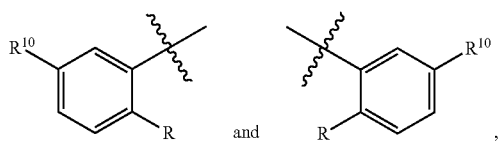

respectively, or

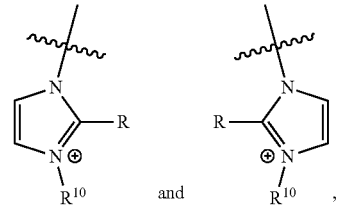

respectively, or

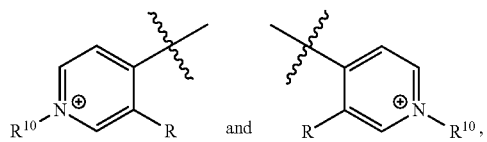

respectively.

In certain embodiments, R$^{10}$ is alkyl (particularly unbranched alkyl or haloalkyl (particularly —CF$_3$)), substituted sulfonyl (particularly sulfonylC$_{1-6}$alkyl), or substituted carboxyl (particularly —COOR where R is alkyl).

In certain embodiments, a is 1 and both R$^{10}$ are the same.

In certain embodiments, at least one R is I. In certain embodiments both R groups are halogen. In certain embodiments, both R groups are I.

Particular examples of the presently disclosed compounds may include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The presently disclosed compounds can have at least one asymmetric center or geometric center, cis-trans center (C═C, C═N). All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}$F, etc.

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

In certain embodiments, the compounds can be made according to the following scheme:
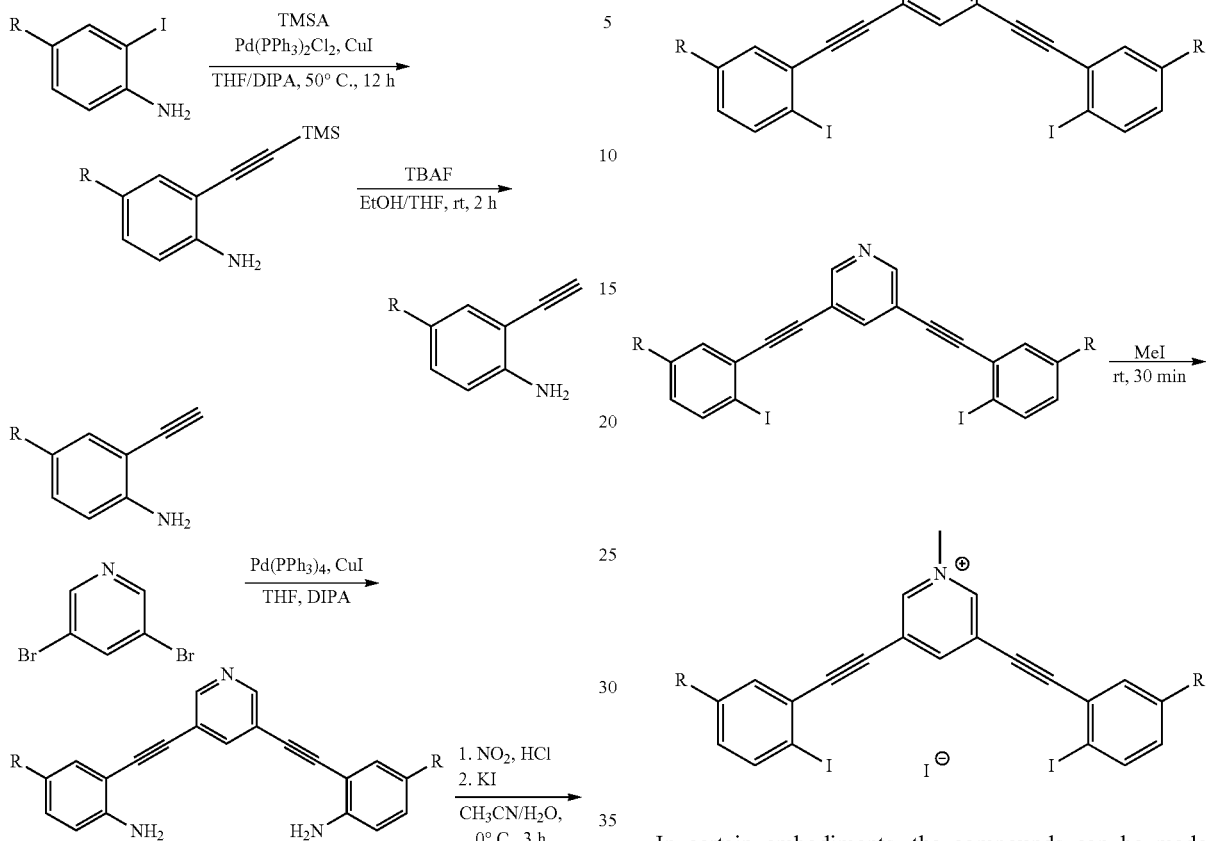
In certain embodiments, the compounds can be made according to the following alternative scheme:
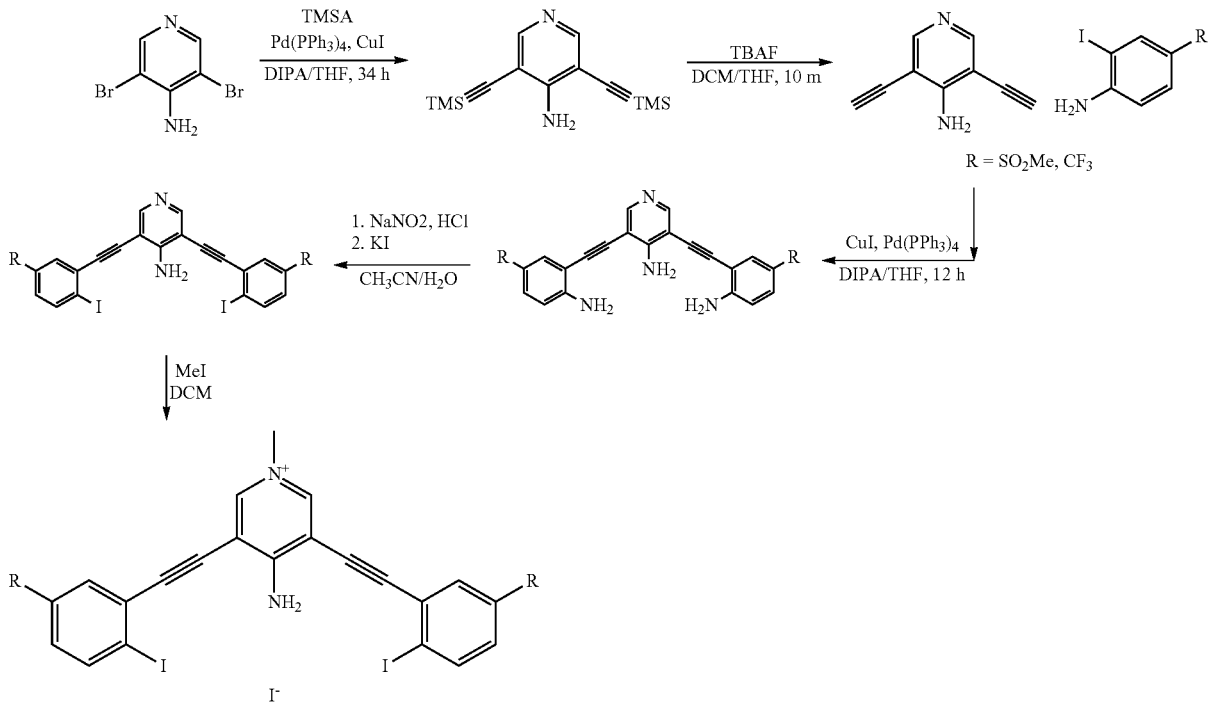

Illustrative compounds are shown below:
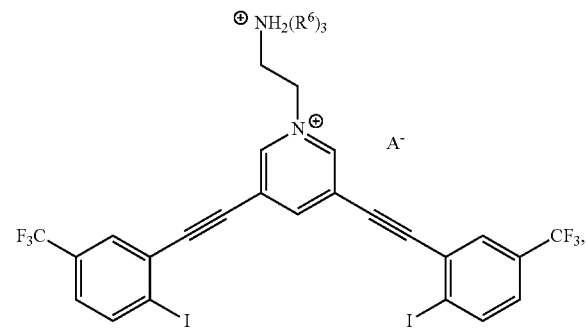
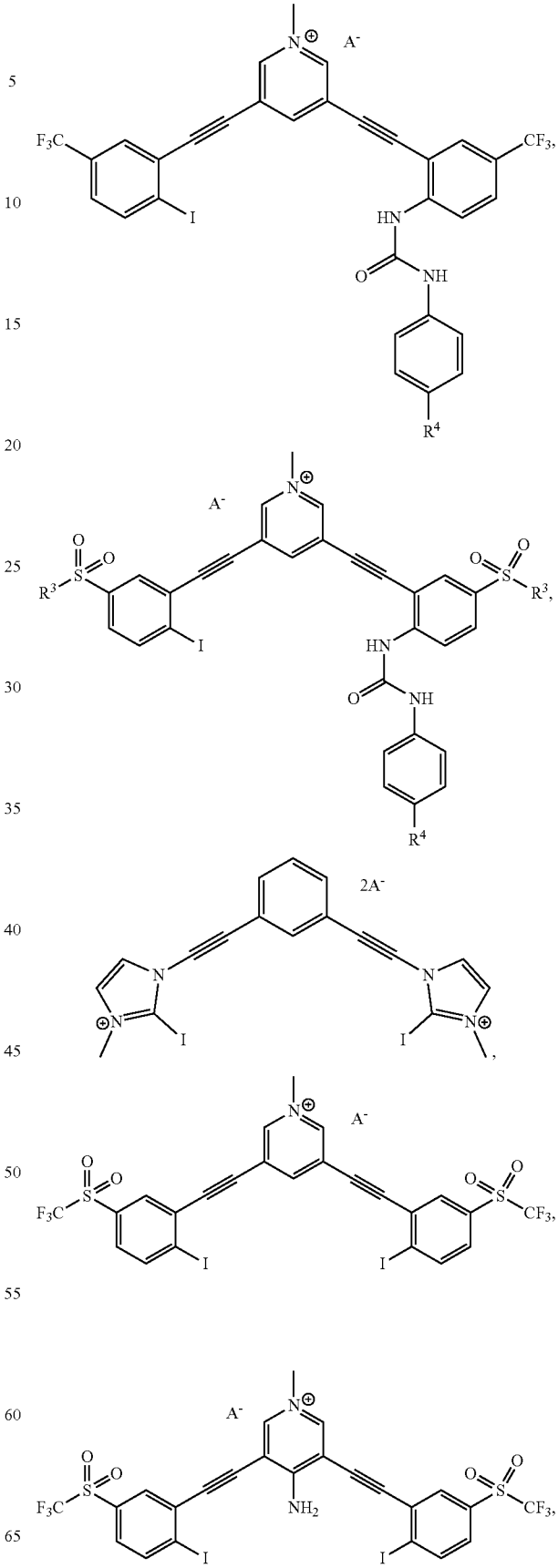

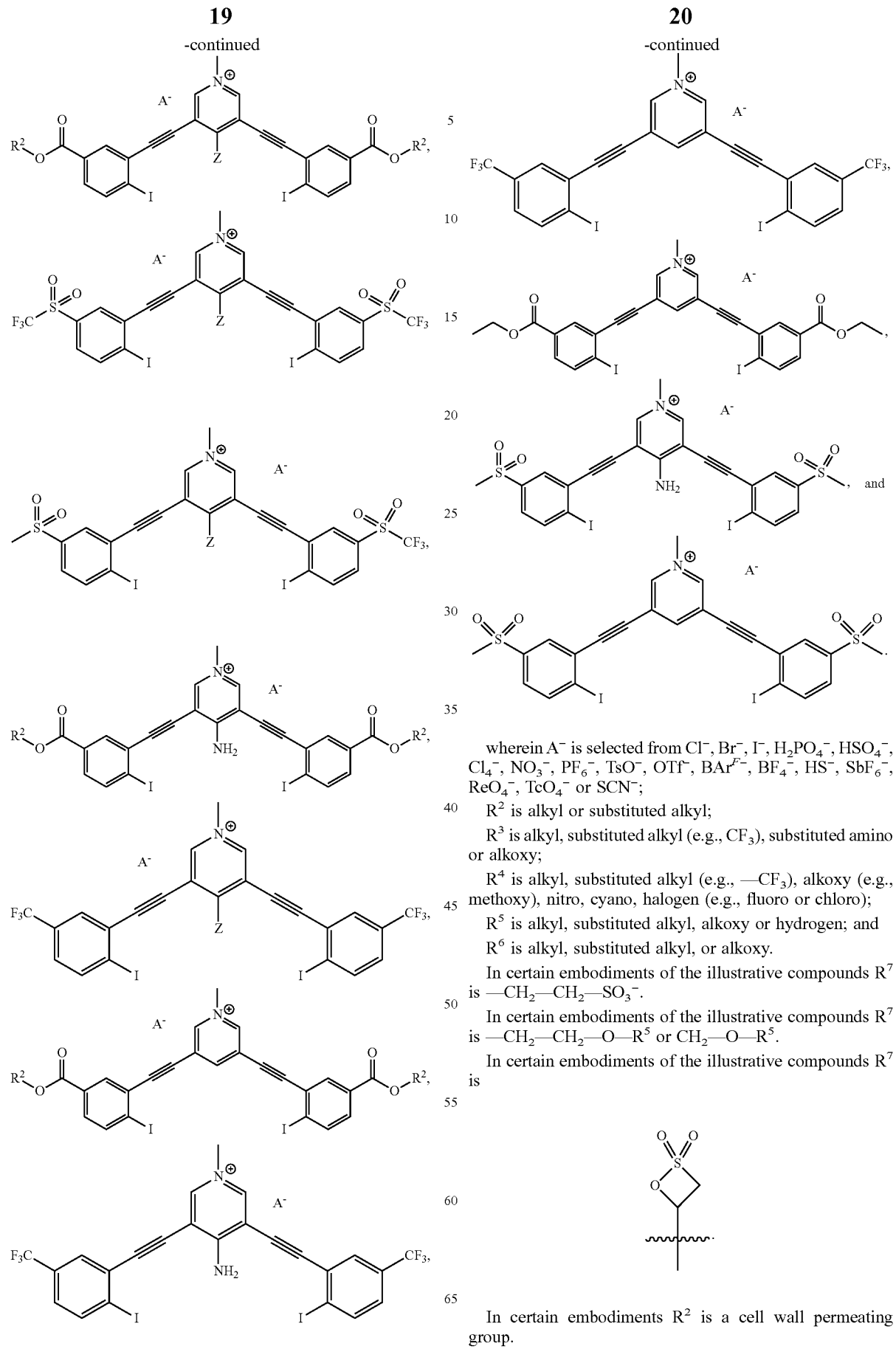

wherein A⁻ is selected from Cl⁻, Br⁻, I⁻, $H_2PO_4^-$, $HSO_4^-$, $Cl_4^-$, $NO_3^-$, $PF_6^-$, TsO⁻, OTf⁻, $BAr^{F-}$, $BF_4^-$, HS⁻, $SbF_6^-$, $ReO_4^-$, $TcO_4^-$ or SCN⁻;

$R^2$ is alkyl or substituted alkyl;

$R^3$ is alkyl, substituted alkyl (e.g., $CF_3$), substituted amino or alkoxy;

$R^4$ is alkyl, substituted alkyl (e.g., —$CF_3$), alkoxy (e.g., methoxy), nitro, cyano, halogen (e.g., fluoro or chloro);

$R^5$ is alkyl, substituted alkyl, alkoxy or hydrogen; and $R^6$ is alkyl, substituted alkyl, or alkoxy.

In certain embodiments of the illustrative compounds $R^7$ is —$CH_2$—$CH_2$—$SO_3^-$.

In certain embodiments of the illustrative compounds $R^7$ is —$CH_2$—$CH_2$—O—$R^5$ or $CH_2$—O—$R^5$.

In certain embodiments of the illustrative compounds $R^7$ is

In certain embodiments $R^2$ is a cell wall permeating group.

Additional illustrative compounds are shown below:
Further illustrative compounds are shown below:
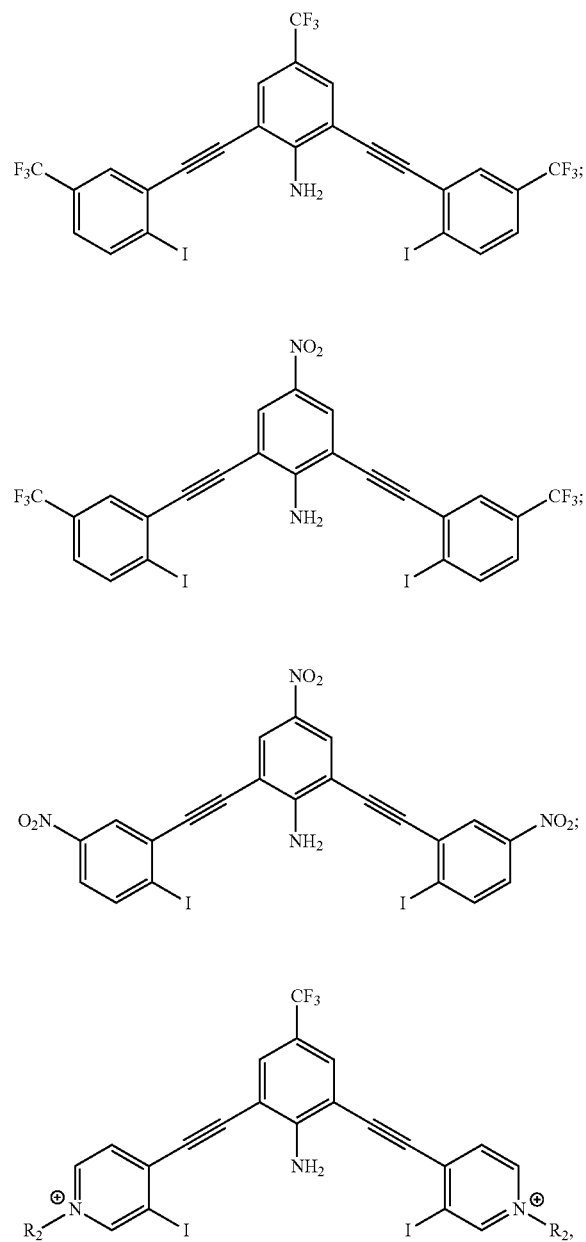
wherein R₂ is methyl or octyl; and
wherein R₂ is methyl or octyl.
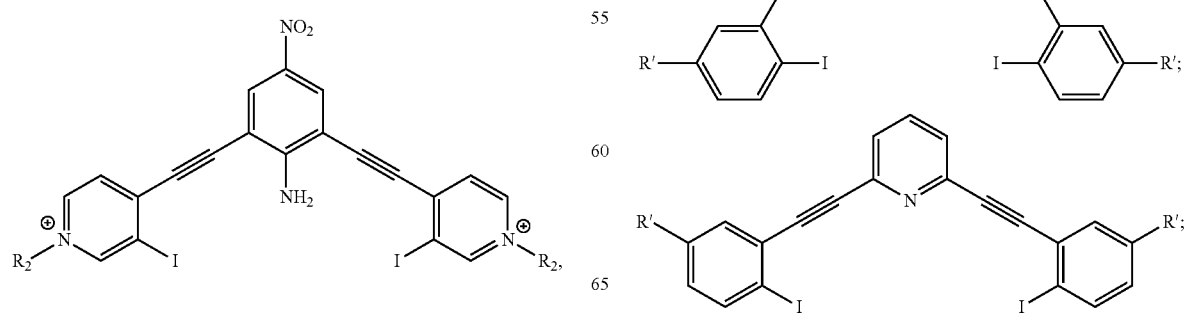

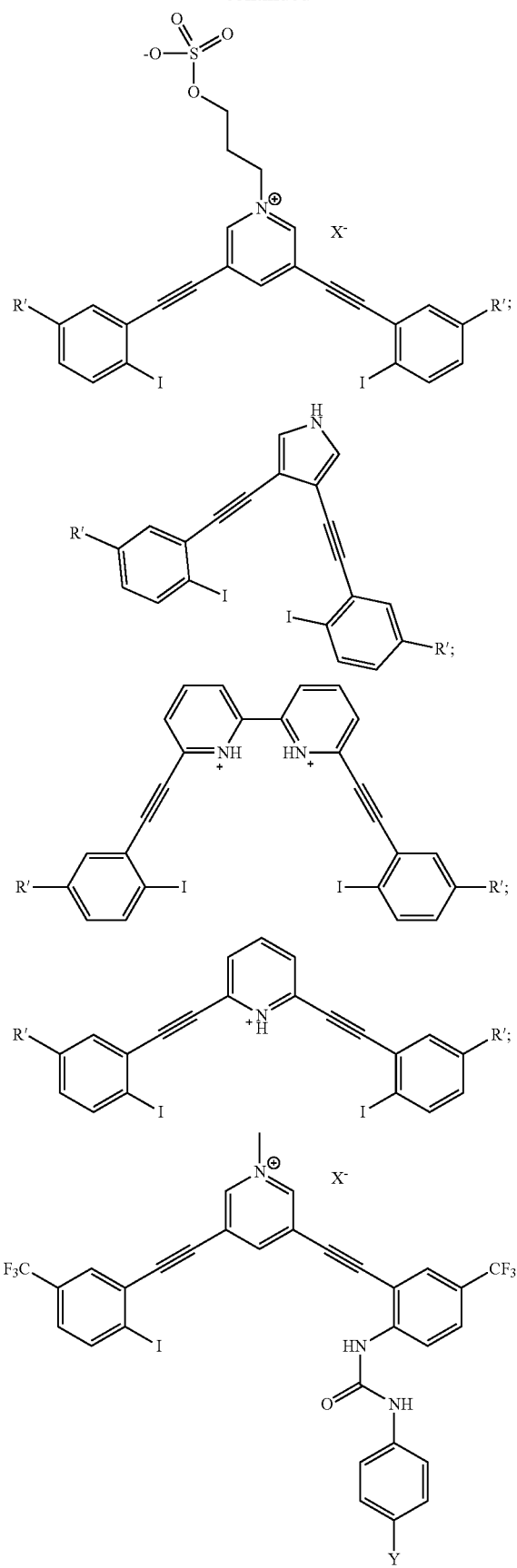
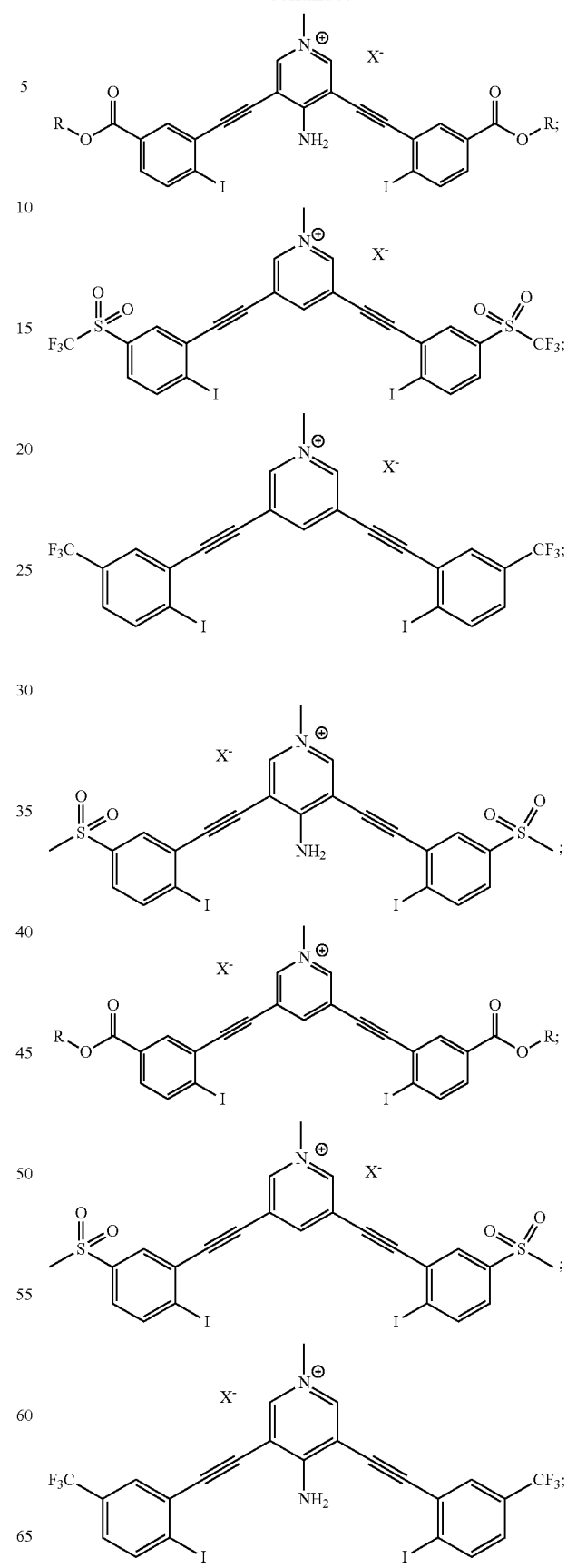

-continued

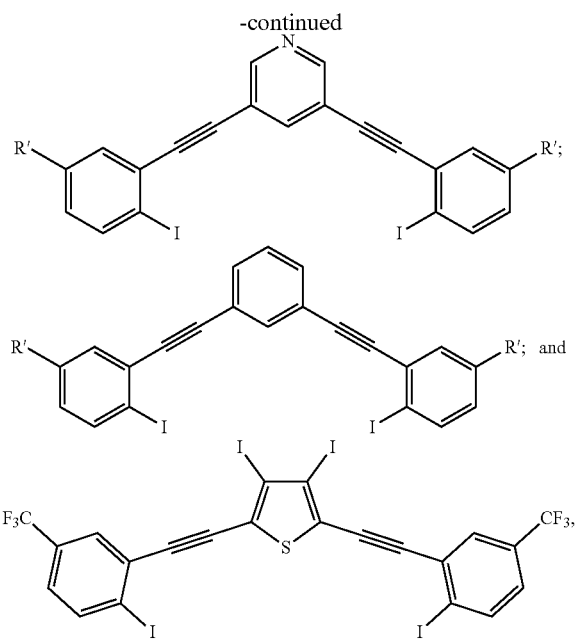

wherein
X⁻ is Cl⁻, Br⁻, I⁻, $H_2PO_4^-$, $HSO_4^-$, $ClO_4^-$, $NO_3^-$, $PF_6^-$, TsO⁻, or OAc⁻;
R' is $CF_3$, $SO_2Me$, $SO_2CF_3$, or $SO_2$(alkyl);
Z is Br or I;
Y is $CF_3$, OMe, or $NO_2$; and
R is Et or Me.

In certain embodiments the compounds of formula I are colorimetric sensors. For example, they may undergo a color change (i.e., from a first color to a second color) and/or gelation in the presence of specific anions (e.g., with halides and perchlorate).

Exemplary receptor compounds exhibit ligand binding selectivity or recognition. The host compounds may exhibit selectivity in binding of an anion or reporting of anion's presence. For example, a spectral property of a host compound, such as fluorescence, may shift upon binding certain ligands, but not others. It has been demonstrated for exemplary compounds disclosed herein that the spectral properties, such as the UV-Vis spectra shift noticeably upon binding of different guests. For example, the extended conjugation inherent in 2,6-bis(2-anilinoethynyl)pyridines derivatives produces distinct emission properties that will be used to monitor interactions with guest molecules.

Typically, for binding anionic ligands, receptor compounds are protonated. Particular examples of anionic ligands bound and/or recognized by the disclosed receptor compounds are ligands that include Cl⁻, Br⁻, I⁻, $H_2PO_4^-$, $HSO_4^-$, $ClO_4^-$, $NO_3^-$, $PF_6^-$, TsO⁻, OTf⁻, $BAr^{F-}$, $BF_4^-$, HS⁻, $SbF_6^-$, $ReO_4^-$, $TcO_4^-$ or SCN⁻. Exemplary receptor compounds exhibit ligand binding selectivity or recognition. The receptor compounds may exhibit selectivity in binding of the ligand or reporting of a ligand's presence. For example, a spectral property of a receptor compound, such as fluorescence, may shift upon binding certain ligands, but not others.

In certain embodiments, the receptor compound may be included within a membrane of an electronic device (e.g., field effect transistor, ion-selective electrode, microfluidic, electrochemical cell, pre-concentration membrane, lab-on-a-chip membrane/component, etc.) to provide an electrical readout of the detection of $H_2S$ or HS⁻.

In one embodiment, the receptor compound is included in a field effect transistor (FET) device.

Several embodiments are described below in the following numbered clauses:

1. A compound, or a protonate or salt thereof, of formula I:

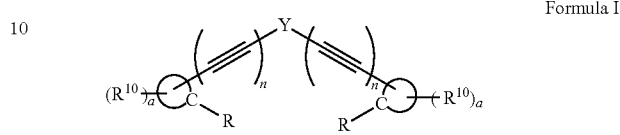

Formula I wherein Y is aryl, substituted aryl, heteroaryl, or substituted heteroaryl;
n is 1 or 2;
each $R^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;
a is 0 to 4;

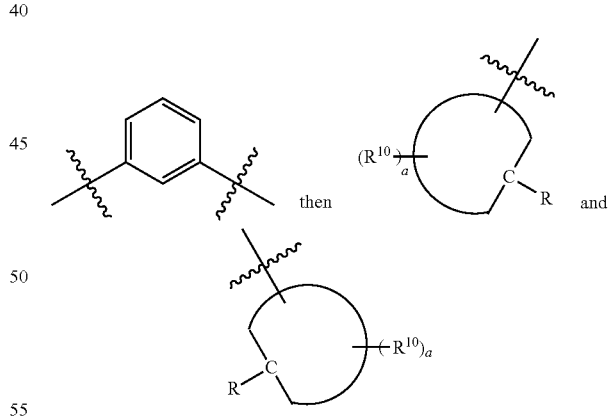

is an aryl or heteroaryl ring; and
each R is independently halogen, carbonylamino, sulfonamide, carboxylic acid or hydrogen, provided at least one R is a halogen; and
provided that if Y is

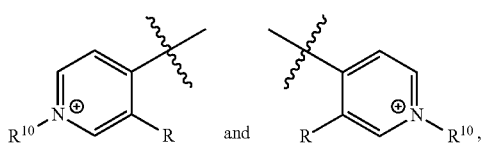

then

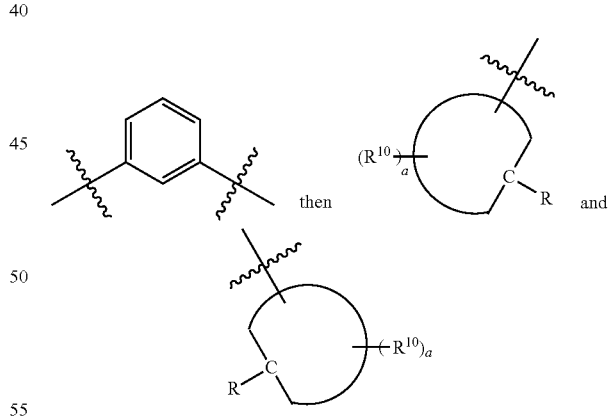 and are not

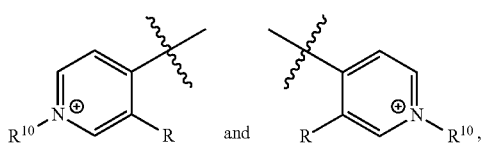

respectively.

2. The compound of clause 1, wherein Y is

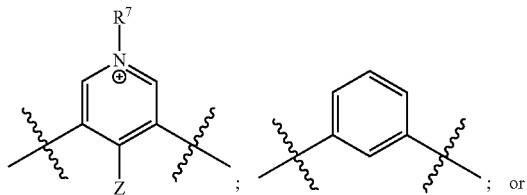; or

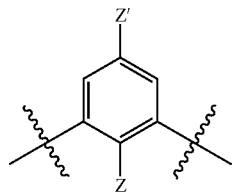

wherein Z is hydrogen, halogen, amino, substituted amino, hydroxy, amido, urea or sulfonamido; Z' is hydrogen, halogen, substituted alkyl (e.g., haloalkyl such as —CF$_3$), nitro, or cyano; and R$^7$ is hydrogen, alkyl, substituted alkyl, or polyethylene glycol.

3. The compound of clause 2, wherein Y is

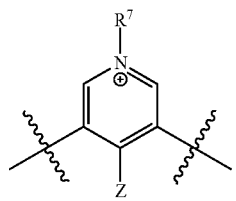

and R$^7$ is C$_1$-C$_6$ alkyl, alkoxyalkyl, aminoalkyl or sulfonylalkyl.

4. The compound of clause 3, wherein R$^7$ is methyl.

5. The compound of any one of clauses 2 to 4, wherein Z is —NH$_2$, —Br, or —I.

6. The compound of clause 2, wherein Y is

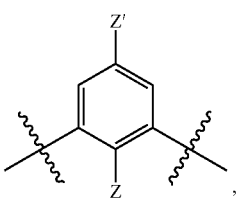

Z is —NH$_2$ and Z' is —F.

7. The compound of any one of clauses 1 to 6, wherein n is 1.

8. The compound of any one of clauses 1 to 7, wherein a is 1.

9. The compound of any one of clauses 1 to 8, wherein the

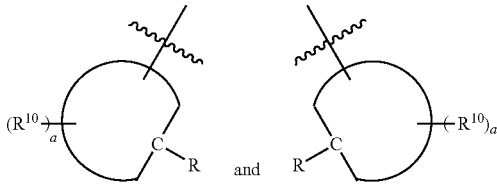

portions of the compound of formula I are:

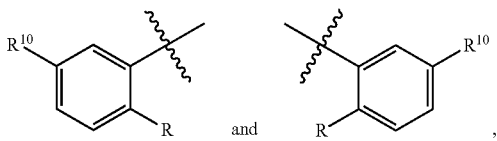

respectively, or

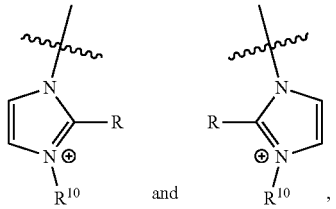

respectively, or

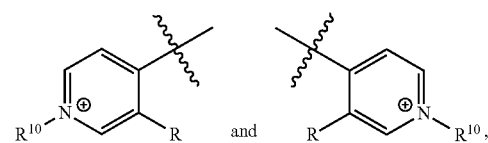

respectively.

10. The compound of any one of clauses 1 to 9, wherein R$^{10}$ is alkyl, substituted alkyl, substituted sulfonyl, or substituted carboxyl.

11. The compound of any one of clauses 1 to 9, wherein R$^{10}$ is unbranched alkyl, —CF$_3$, sulfonylC$_{1-6}$alkyl, or —COOR wherein R is alkyl.

12. The compound of any one of clauses 1 to 11, wherein a is 1 and both R$^{10}$ are the same.

13. The compound of any one of clauses 1 to 12, wherein at least one R is —I.

14. The compound of any one of clauses 1 to 12, wherein both R groups are —I.

15. The compound of any one of clauses 1 to 14, wherein the compound is protonated.

16. A compound, or a protonate or salt thereof, of formula II:

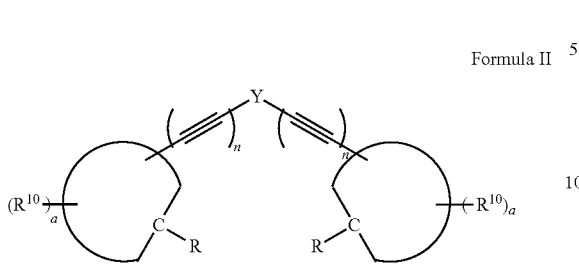

Formula II wherein Y is

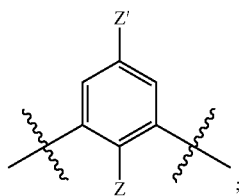

wherein Z is hydrogen, halogen, amino, substituted amino, hydroxy, amido, urea or sulfonamido; Z' is hydrogen, halogen, substituted alkyl (e.g., haloalkyl such as —CF$_3$), nitro, or cyano, provided Z and Z' are not both hydrogen;

n is 1 or 2;

each R$^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;

a is 0 to 4;

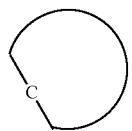

is an aryl or heteroaryl ring; and each R is independently halogen, carbonylamino, sulfonamide, carboxylic acid or hydrogen;

and the

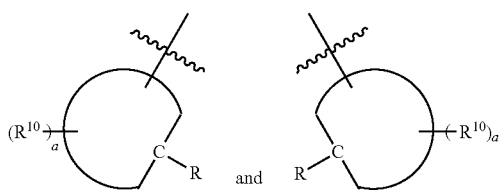

portions of the compound of formula II are

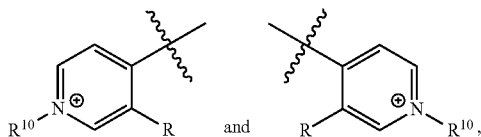

respectively.

17. The compound of clause 16, wherein Z is —NH$_2$ and Z' is F.

18. The compound of clause 16 or 17, wherein both R groups are —I.

19. The compound of clause 16 or 17, wherein both R groups are hydrogen.

20. A receptor-ligand structure comprising the compound of any one of clauses 1 to 19 as a receptor and a ligand.

21. A receptor-ligand structure comprising the compound of any one of clauses 1 to 19 as a receptor and a ligand that includes at least one anion selected from Cl$^-$, Br$^-$, I$^-$, H$_2$PO$_4^-$, HSO$_4^-$, ClO$_4^-$, NO$_3^-$, PF$_6^-$, TsO$^-$, OTf$^-$, BAr$^{F-}$, BF$_4^-$, HS$^-$, SbF$_6^-$, ReO$_4^-$, TcO$_4^-$ or SCN$^-$.

22. A method for detecting for the presence of an anion in a system, comprising contacting a sample from the system with a compound, or a protonate or salt thereof, of any one of clauses 1 to 19.

EXAMPLE A

Design and Synthesis of 1,3-bis(4-ethynylpyridinium) Receptors.

Figure 1D:
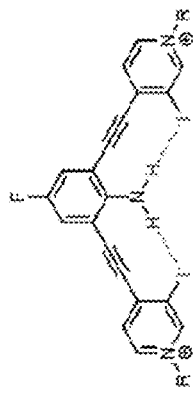
Figures 2A, 2B, 2C:
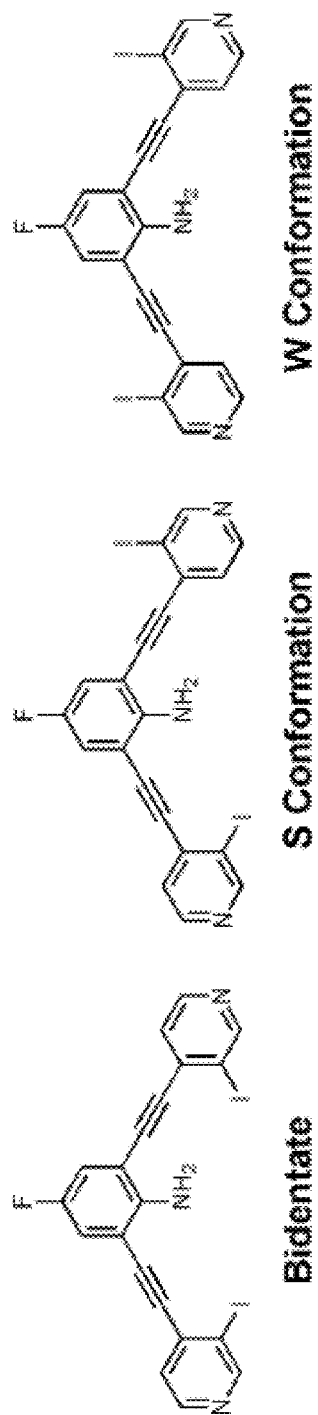
FIGS. 2A-C are ChemDraw representations of the three planar conformations obtained by rotating about the alkyne bonds: the bidentate conformation (left), where both XB donors are convergent; the S conformation (middle), where the XB donors are on opposite sides of the molecule; and the W conformation (right), where both XBs are directed away from the amine.

A bisethynyl receptor that binds anions and neutral Lewis bases with two iodopyridinium XB donors was previously developed (Massena et al, Chem. Commun., 2015, 51, 1417-1420; Rid et al, Acta Crystallogr. Sect. B. Struct. Sci. Cryst. Eng. Mater., 2017, 73, 203-209). The alkynes promote rigidity and directionality, but their low rotational barrier allows the receptors to adopt three planar binding conformations (FIG. 2). Preorganization could be accomplished by HBing to the electron-rich belt of the XB donors with an electron-deficient aniline (FIG. 1D). These second-generation receptors are referred to as G2XB and G2HB (Scheme 1 below).

The synthesis of G2XB, G2HB and G2XBme is outlined in Scheme 1 below. 2,6-bis(ethynyl)-4-fluoroaniline (2) was synthesized by Sonogashira cross-coupling 2,6-dibromo-4-fluoroaniline with trimethylsilylacetylene followed by removal of the trimethylsilyl protecting groups. Precursors 3 and 5 were synthesized by Sonogashira cross coupling 2 at the iodo-functionality of 3-bromo-4-iodopyridine or 4-iodopyridine, respectively. The XB donor iodines of 4 were installed by microwave assisted halogen exchange of 3. Alkylation of the pyridines with octyl triflate activated the XB and HB donors of 4 and 5 respectively and enabled organic solubility. Anion metathesis of the triflate (OTf$^-$) counteranions for noncoordinating tetrakis(3,5-bis(trifluoromethyl)phenyl)borate (BAr$^{F-}$)anions produced G2XB and G2HB (see ESI). The methyl derivative, G2XBme, was similarly synthesized for X-ray diffraction studies. G1XB, G1HB and G1XBme were synthesized as previously reported. (Massena et al, Chem. Commun., 2015, 51, 1417-1420)

Scheme 1. Synthesis of G2XB, G2HB and G2XBme receptors.

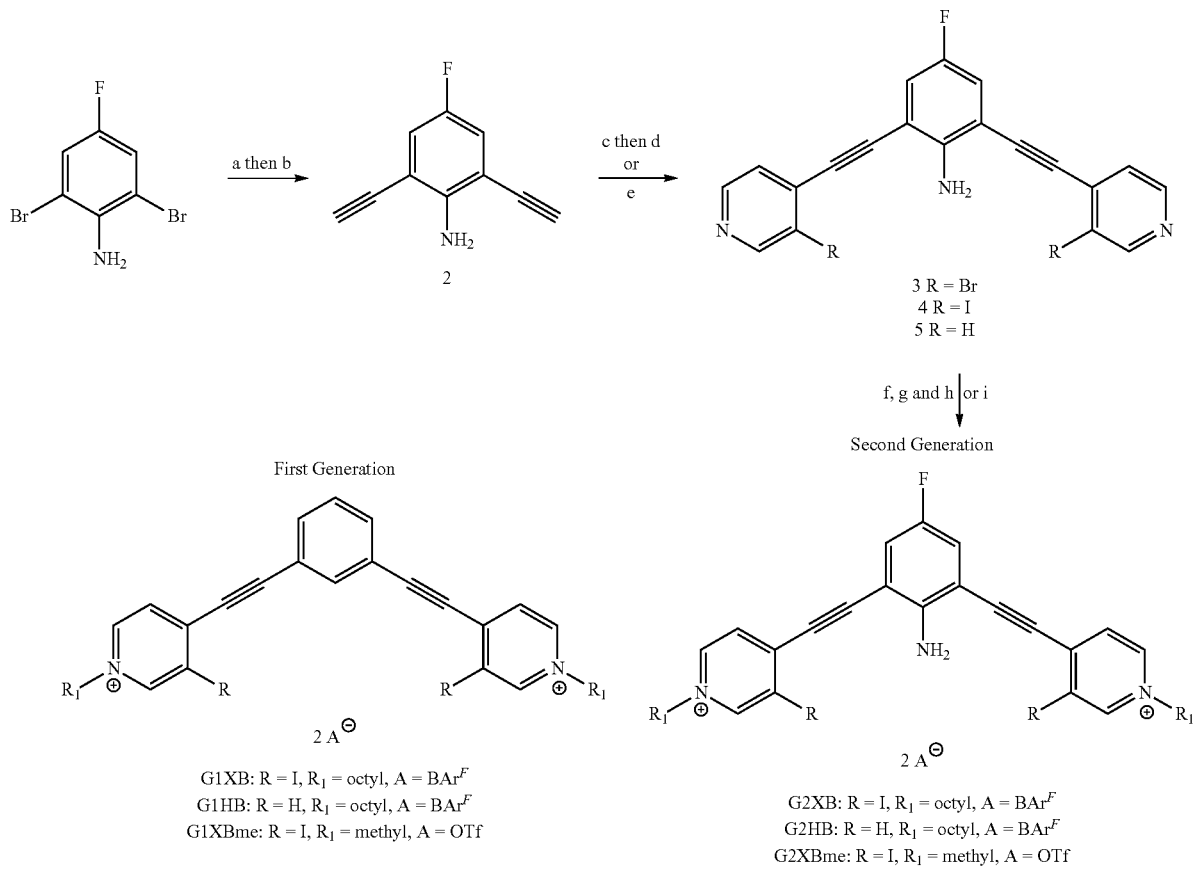

G1XB: R = I, R$_1$ = octyl, A = BAr$^F$
G1HB: R = H, R$_1$ = octyl, A = BAr$^F$
G1XBme: R = I, R$_1$ = methyl, A = OTf G2XB: R = I, R$_1$ = octyl, A = BAr$^F$
G2HB: R = H, R$_1$ = octyl, A = BAr$^F$
G2XBme: R = I, R$_1$ = methyl, A = OTf Reagents and conditions: (a) TMS-acetylene, Pd(PPh$_3$)$_2$Cl$_2$, Cu(I)I, DIPEA, DMF, overnight, N$_2$, 60° C., 90%; (b) K$_2$CO$_3$, MeOH/DCM (1:1 v/v), 4 hours, rt, 73%; (c) 3-bromo-4-iodopyridine, Pd(PPh$_3$)$_2$Cl$_2$, Cu(I)I, DIPEA, DMF, overnight, N$_2$, rt, 90%; (d) NaI, Cu(I)I, 1,4-dioxane, trans-N, N'-dimethylcyclohexane-1,2-diamine, microwave reactor, 150° C., 5.5 hours, 81%; (e) 4-iodopyridine, Pd(PPh$_3$)$_2$Cl$_2$, Cu(I)I, DIPEA, DMF, overnight, N$_2$, 60° C., 58%; (f) octyl triflate, DCM, rt, overnight, 54%; (g) TBA$^+$Cl$^-$, MeCN, overnight, 77%; (h) Na$^+$BAr$^{F-}$, DCM, rt, overnight, 63%; (i) methyl triflate, DCM, rt, overnight, 89%.

Solution Assessment of HB-XB Preorganization and Enhanced XB $^1$H NMR titrations were conducted to probe intramolecular HB-XB preorganization and XB enhancement in G2XB (Table 1). Association constants were determined by HypNMR 2008 for each receptor and the tetra-n-butylammonium (TBA$^+$) halides (Cl$^-$, Br$^-$ and I$^-$). All titrations were performed in 60% CD$_3$NO$_2$/40% CDCl$_3$ at 25° C. to ensure solubility and to prevent the binding constants from exceeding the limit of NMR. Both XB receptors, G2XB and G1XB, exhibit anion-induced upfield pyridinium proton shifts, characteristic of XBing in solution. In contrast, the pyridinium protons of the HB receptors, G2HB and G1HB, only shifted downfield, consistent with HBing in solution (see ESI).

Intramolecular HB-XBs enhance halide binding by nearly 9-fold over G1XB, which lacks intramolecular HB-XBs. The halide K$_{11}$ values for G2XB are 23652 M$^{-1}$ for Cl$^-$, 32888 M$^{-1}$ for Br$^-$ and 36943 M$^{-1}$ for I$^-$. In contrast, G1XB binds halides much more weakly with K$_{11}$ values of 2629 M$^{-1}$ for Cl$^-$, 4688 M$^{-1}$ for Br$^-$, and 4384 M$^{-1}$ for I$^-$. Additionally, both G2XB and G1XB prefer larger halides (I$^-$≈Br$^-$>Cl$^-$) which could be attributed to the size selective binding pocket and HSAB complementarity of the XB.[83-88] The second binding event (K$_{12}$) is quite weak for all receptors and likely represents non specific ion pairing to balance the charge.

To verify that the amine forms intramolecular HBs instead of HBing directly with the anions, the binding of G2XB was compared with three control receptors. G2XB binds halides more than an order of magnitude greater than G2HB, which contains the amine but lacks XB donors. The K$_{11}$ values for G2HB are 2503 M$^{-1}$ for Cl$^-$, 2108 M$^{-1}$ for Br$^-$, and 1753 M$^{-1}$ for I$^-$. Furthermore, the amine of G2HB marginally increases binding for both Br$^-$ and I$^-$ and even decreases Cl$^-$ binding when compared to G1HB, which lacks both the amine and fluorine (G1HB K$_{11}$ values of 9043 for Cl$^-$, 1145 for Br$^-$, and 1031 M$^{-1}$ for I$^-$). Thus, the amine does not significantly HB to the halides in this system.

Comparing the binding of G2HB to G1XB establishes that the XB is more effective at binding Br$^-$ and I$^-$ than the HBs in G2HB. The K$_{11}$ values of G1XB (4688 M$^{-1}$ for Br$^-$ and 4384 M$^{-1}$ for I$^-$) are more than double the K$_{11}$ values of G2HB (2108 M$^{-1}$ for Br$^-$ and 1753 M$^{-1}$ for I$^-$). Collectively these studies support that intramolecular HB-XBs preorganizes the receptor and significantly enhances halide binding.

NMR analysis of chemical shifts, hydrogen/deuterium (H/D) exchange rates, and rotational barriers can provide solution evidence of intramolecular HBs to strong acceptors. In contrast, there is a deficiency of NMR studies on HBing to weak organic halogen acceptors. Chemical shift analysis and H/D exchange experiments on this system support that intramolecular HBing occurs in G2XB. The NH$_2$ $^1$H NMR resonance in G2XB was shifted downfield by 0.52 ppm (5.30 ppm, CDCl$_3$) as compared to G2HB (4.78 ppm, CDCl$_3$). The downfield resonance in G2XB is indicitive of deshielded protons which suggest that intramolecular HBing is occuring. H/D exchange experiments were conducted on G2XB and G2HB. G2XB had a slower H/D exchange than G2HB, which is attributed to intermolecular HBing and increased steric interactions in G2XB (see ESI). Additionally, variable temperature (VT) $^1$H NMR was used to evaluate intramolecular HBing. Upon warming, the NH$_2$ signals for both G2XB and G2HB shift upfield. However, the shift in G2XB is slightly more upfield (see ESI), consistent with intramolecular HBing. Together, the solution studies demonstrate that intramolecular HB-XB preorganization is operable and contributes to the improved halide recognition.

tion, highlighting the critical proximity of the HBing amine (see ESI). Notably, addition of the intramolecular HBs increases the rotational barrier between the bidentate and S conformation by 1.64 kcal/mol. Both single point energy and alkyne conformational driving studies further support the hypothesis that HB-XB preorganizes bidentate XB conformations of G2XB.

Figures 4A, 4B, 4C, 4D:
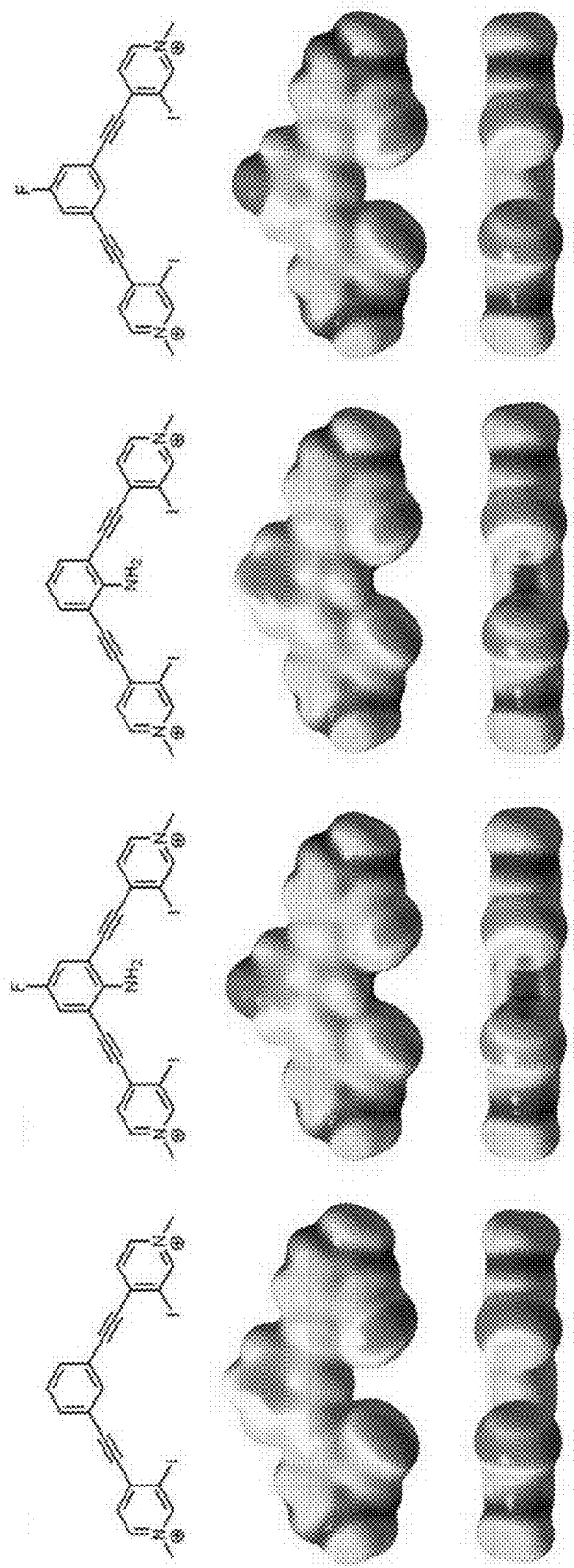
FIG. 4 shows ChemDraw and ESP maps of G1XBme$^{2+}$ (a), G2XBme$^{2+}$ (b), G2XBme$^{2+}$ with no fluorine (c) and G2XBme$^{2+}$ with no amine (d). All ESP maps are displayed on the same scale. Electron-deficient regions are blue and electron rich regions are red.

Computations were also used to model how the intramolecular HB influences the strength of the XB. The effect is illustrated by electrostatic potential (ESP) maps of G1XBme$^{2+}$, G2XBme$^{2+}$, and two derivatives of G2XBme$^{2+}$ (FIG. 4). G2XBme$^{2+}$ (FIG. 4b) has a larger, more electrophilic region at the σ-hole than G1XBme$^{2+}$ (FIG. 4a). This augmentation is attributed to the additional polarization by the intramolecular HB. The HB further polarizes the electron density around the halogen which strengthens the XB interaction.$^{§§§§§§}$ Additional calculations verify that the fluorine

TABLE 1

Association Constants for G2XB, G2HB, G1XB and G1HB with halides.

| | G2XB | | G1XB | | G2HB | | G1HB | |
|---|---|---|---|---|---|---|---|---|
| | $K_{11}$ (M$^{-1}$) | $K_{12}$ (M$^{-1}$) | $K_{11}$ (M$^{-1}$) | $K_{12}$ (M$^{-1}$) | $K_{11}$ (M$^{-1}$) | $K_{12}$ (M$^{-1}$) | $K_{11}$ (M$^{-1}$) | $K_{12}$ (M$^{-1}$) |
| Cl$^-$ | 23652 | 25 | 2629 | 37 | 2503 | 47 | 9043 | 38 |
| Br$^-$ | 32888 | 35 | 4688 | 32 | 2108 | 44 | 1145 | 38 |
| I$^-$ | 36943 | 28 | 4384 | 28 | 1753 | 44 | 1031 | 33 |

The $K_{11}$ and $K_{12}$ values are reported as the average of three titration experiments. All titrations were performed in 40% CDCl$_3$/60% CD$_3$NO$_2$; errors are estimated at 10%. Tetra-n-butylammonium halides were used and titrations were performed at 25°C. HypNMR 2008 was used to fit changes in chemical shift to a stepwise 1:1 and a 1:2 host-guest binding model. Continuous refinements of multiple isotherms provided stability constants ($K_a$) for all host-guest complexes in solution.

Computational Evaluations of Receptor Conformations and XB Enhancement

Gas-phase density functional theory (DFT) calculations further quantified the role of intramolecular HB-XBing in preorganization and XB augmentation. To simplify calculations, three planar conformations of G2XBme$^{2+}$ were evaluated. Calculations were performed with the B3LYP functional using the Gaussian 09 suite of programs. The 6–31+G(d,p) basis set was employed for all atoms except nitrogen and iodine. To appropriately account for the HB donor the aug-cc-pVTZ basis set was used for nitrogen. To model the polarizable iodine the LANL2DZdp and effective core potential (ECP) was used. The LANL2DZdp ECP basis set was downloaded from the EMSL Basis Set Exchange. Crystal structures were used as starting positions for all calculations. Optimized geometries and frequencies were calculated to confirm molecules were at local minima (details in ESI).

Single point energy calculations of G2XBme$^{2+}$ illustrate that intramolecular HB-XBs stabilize the receptor (FIG. 3). The number of intramolecular HB-XBs directly correlates with receptor stability. The bidentate conformation, with two intramolecular HBs, is more stable than the W conformation (no HB-XB) by 1.29 kcal/mol. The S conformation, with one intramolecular HB contact, is less stable than the bidentate conformation by 0.61 kcal/mol. The W conformation, lacking intramolecular HB-XBs, is the least stable and is 0.68 kcal/mol higher in energy than the S conformation.

To further analyze how intramolecular HBs stabilize G2XB, conformational analysis about the alkynes of G2XBme$^{2+}$ and G1XBme$^{2+}$ were examined G2XBme$^{2+}$ favors the bidentate conformation over the S conformer by over 0.60 kcal/mol which is comparable to the single point energy calculations. In contrast, G1XBme$^{2+}$ favors the S conformer by 0.16 kcal/mol over the bidentate conformaatom is not the cause of this effect. The derivative of G2XBme$^{2+}$ without the fluorine (FIG. 4c) has a similar σ-hole to G2XBme$^{2+}$. However, when the amine is removed but the fluorine is retained, the σ-hole is markedly reduced (FIG. 4d).

The magnitude by which HBing enhances bidentate XBing in this system was evaluated by computing gas-phase interaction energies with Br$^-$. The interaction energy is computed as the difference between the complex and the isolated consituents in the same geometry as the complex (see ESI). G2XBme$^{2+}$ and the derivative of G2XBme$^{2+}$ with no amine (no HB-XBs), were compared. The presence of the amine in G2XBme$^{2+}$ strengthened the bidentate XB interaction by more than 3.23 kcal/mol over the receptor with no HB-XB. Together, these calculations corroborate the solution data and the dual role of the HB-XB to enhance the σ-hole and promote preorganization.

HB-XB Impact on Solid-State Features

The intramolecular HB-XBs in G2XBme$^{2+}$ promote the bidentate conformation. In contrast, previous solid-state studies of G1XBme$^{2+}$ produced structures with multiple conformations. Here, we present crystal structures of G2XBme$^{2+}$, G2XB$^{2+}$, and G1XBme$^{2+}$ that illustrate intramolecular HB-XBs facilitate planar conformations with stronger XB contacts for anion recognition. The receptors crystallize in the bidentate conformation with every halide, allowing direct comparison of the XB contacts and geometries of each receptor (crystal growth conditions and details in ESI).

Bidentate XB Structures

Figure 5B:
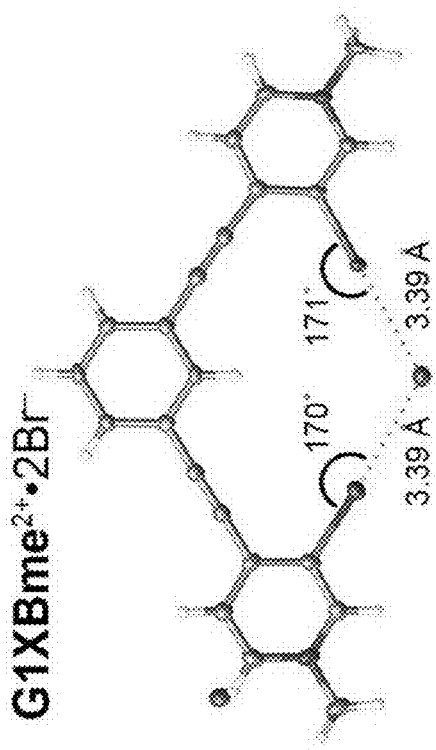
FIGS. 5A-B show bidentate XBing conformations of G2XBme$^{2+}$•2Br$^-$ (left) and G1XBme$^{2+}$•2Br (right). XB distances and angles are displayed. Thermal ellipsoids are drawn at the 50% probability level. G1XBme$^{2+}$•2Br$^-$ crystallized with a methanol molecule which HBs with noncoordinating Br$^-$ and is omitted for clarity.
Figure 5A:
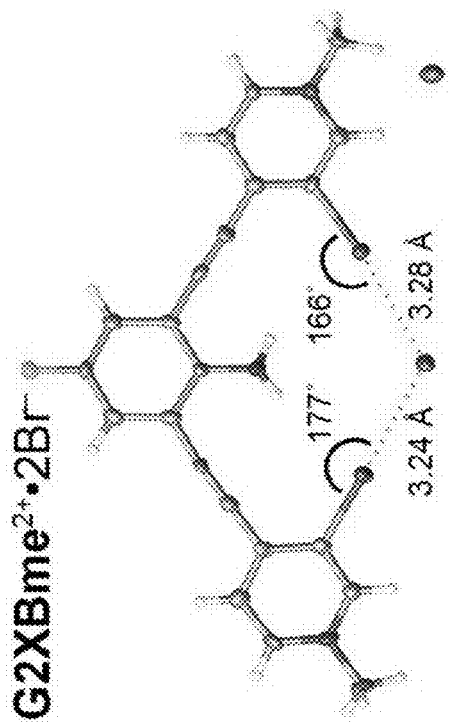

Both G2XBme$^{2+}$ and G1XBme$^{2+}$ crystallized with Br$^-$ (FIG. 5) forming bidentate XB interactions with one Br$^-$. As designed, G2XBme$^{2+}$ forms intramolecular HBs that influence both the receptor conformation and the strength of the XB. The intramolecular HBs in G2XBme$^{2+}$•2Br$^-$ have N—H•••I distances and angles of 2.96(10) Å, 165(6)° and 3.14(14) Å, 155(5)°. The amine protons preorganize the complex of G2XBme$^{2+}$•2Br resulting in pyridnium rings that twist out of coplanarity with the fluoroaniline core by only 4.8(2) and 7.8(2)°. In contrast, G1XBme$^{2+}$•2Br$^-$ which lacks intramolecular HBs, is more distorted, with the pyridinium rings twisting out of coplanarity with the benzene core by 15.18(12) and 14.13(12)°. Additionally, the intramolecular HBs strengthen the XB. The XB distances and angles in G2XBme$^{2+}$•2Br$^-$ are shorter and more linear with values of 3.2358(11) Å, 176.86(19)° and 3.2787(11) Å, 166.78(19)° ($R_{IBr}$ values of 0.82 and 0.83). The distances and angles of G1XBme$^{2+}$•2Br$^-$ are longer at 3.3938(5) Å, 169.9(1)° and 3.3905(5) Å, 171.13(10)° ($R_{IBr}$ values of 0.87 and 0.87). The second Br anion in both structures interacts with other receptor molecules through C—H HB and ion-pairing to balance the two positive charges associated with the receptor. The significant reduction (up to 0.158 Å) in HB-XB (G2XBme$^{2+}$•2Br$^-$) distance over the nonHB-XB (G1XBme$^{2+}$•2Br$^-$) supports the HB-XB enhancement observed in the computational and solution studies.

Figure 6B:
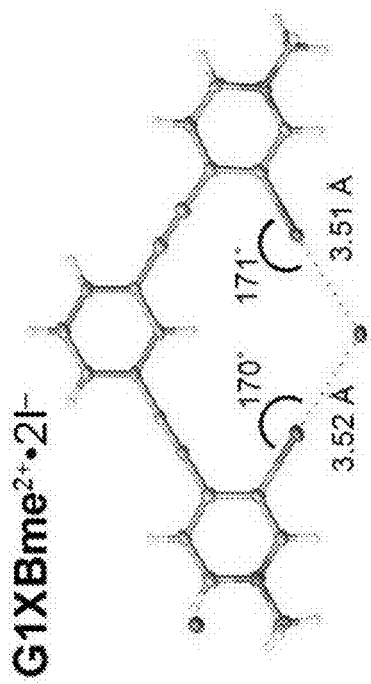
FIGS. 6A-B show bidentate XB conformations of G2XB$^{2+}$•2I$^-$ (left) and G1XBme$^{2+}$•2I$^-$ (right). XB distances and angles are displayed. Thermal ellipsoids are drawn at the 50% probability level. G1XBme$^{2+}$•2I$^-$ crystallized with a methanol molecule which exhibits HBing with noncoordinating I$^-$ and is omitted for clarity.
Figure 6A:
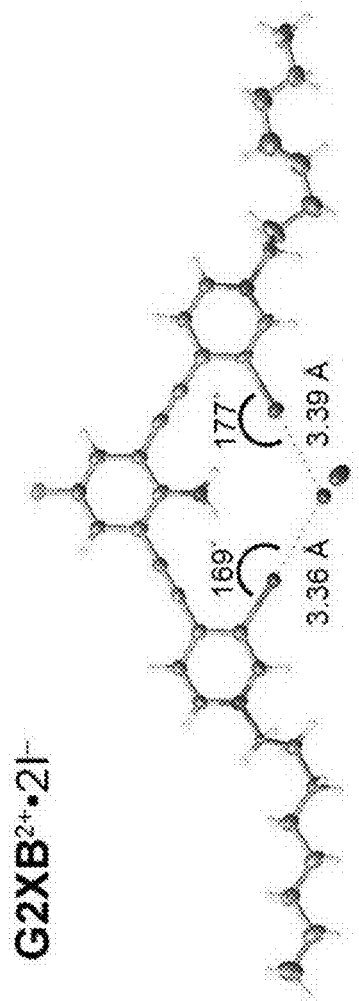

Crystals of G2XB$^{2+}$ and G1XBme$^{2+}$ were also obtained with I$^-$ (FIG. 6) and the structural features parallel the Br$^-$ complexes. Both G1XBme$^{2+}$ and G2XB$^{2+}$ form bidentate XB interactions with one I$^-$. Again, G2XB$^{2+}$ forms intramolecular HBs to both XB iodine donors in G2XB$^{2+}$•2I$^-$ with N—H•••I distances and angles of 2.94(13) Å, 168(8)° and 3.00(7) Å, 170(8)°. These HBs preorganize the complex of G2XB$^{2+}$•2I$^-$ resulting in pyridinium rings that twist out of coplanarity with the fluoroaniline core by only 2.4(3) and 2.8(3)°. In comparison, the pyridinium rings of G1XBme$^{2+}$•2I$^-$ deviate from planarity with the core benzene by 14.0(2) and 14.8(2)°. Again, the HB-XBs produce closer, stronger XB contacts with the anion. The XB distances and angles in G2XB$^{2+}$•2I$^-$ are 3.363(11) Å, 168.7(3)° and 3.3865(11) Å, 176.9(2)° ($R_{II}$ values are 0.82 and 0.83). The weaker XBs in G1XBme$^{2+}$•2I$^-$ have distances and angles of 3.5235(6) Å, 169.82(19)° and 3.5085(7) Å, 170.70(16)° ($R_{II}$ values are 0.87 and 0.86). Also, the second I$^{31}$ anion in both systems interacts with other receptor molecules through C—H HB and ion-pairing to balance the two positive charges associated with the receptor. The nearly 0.16 Å reduction in the XB contacts and more planar conformations in G2XB$^{2+}$ over G1XBme$^{2+}$ support that intramolecular HB-XBs facilitate preorganization and XB enhancement.

Figure 7:
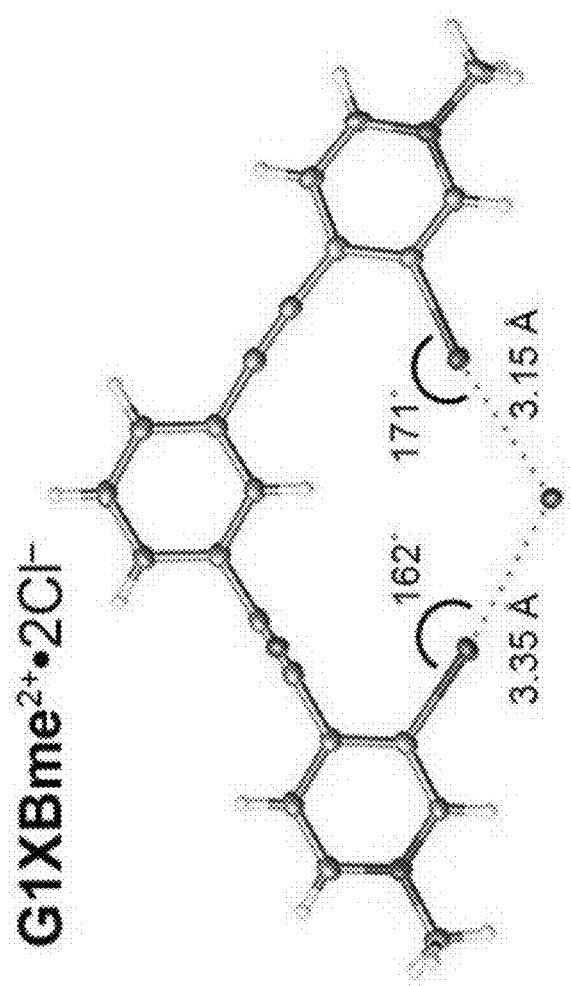
FIG. 7 shows bidentate binding conformation of G1XBme$^{2+}$•2Cl$^-$. XB distances and angles are displayed. Thermal ellipsoids are drawn at the 50% probability level.

A bidentate structure with Cl$^-$ was also obtained for G1XBme$^{2+}$ but not G2XBme$^{2+}$ (FIG. 7). The XB distances and angles are 3.1530(9) Å, 171.08(9)° and 3.3527(9) Å, 162.19(9)° ($R_{ICl}$ values of 0.82 and 0.87). The second anion is held above the complex through C—H HB and ion-pairing that help balance the two positive charges associated with the receptor. The pyridinium rings of G1XBme$^{2+}$•2Cl$^-$ are twisted out of planarity with the benzene core by 3.83(11) and 8.33(11)°. This structure is more planar than the Br$^-$ and I$^-$ structures of G1XBme$^{2+}$. In contrast, the XBs of G1XBme$^{2+}$+.2Cl$^-$ are not as linear as G2XB$^{2+}$ and G2XBme$^{2+}$.

Monodentate XB Structures

Crystallization with the OTf$^-$ anion induces monodentate XBing for both G2XBme$^{2+}$ and G1XBme$^{2+}$. However, G2XBme$^{2+}$•2OTf$^-$, with intramolecular HBs crystallizes in both the bidentate (FIG. 8a) and monodentate S conformation (FIG. 8b) (≈250/50 disorder). The bidentate conformer of G2XBme$^{2+}$•2OTf contains one OTf molecule in the binding pocket that accepts two XBs to two separate oxygen atoms. The amine HBs to the XB donors with N—H•••I distances and angles of 2.9672(6) Å, 168.1(2)° and 3.0546 (3) Å, 166.5(3)°. The bidentate XB distances and angles are 3.195(10) Å, 172.7(3)° and 3.280(9) Å, 148.4(2)° ($R_{IO}$ values of 0.90 and 0.93).

The monodentate S conformer of G2XBme$^{2+}$•2OTf$^-$ provides a unique comparison of two types of XB donors within the same structure, one that accepts an amine HB (HB-XB) and one that does not. The HB-XB donor forms a stronger XB to the OTf$^-$ with a distance and angle of 2.908(8) Å, 175.91(18)° ($R_{IO}$ value of 0.82). Whereas the other XB has a distance and angle of 3.089(6) Å, 168.1(2)° ($R_{IO}$ value of 0.87). The greater than 0.18 Å reduction in XB distance (between the HB-XB and nonHB-XB donors) is comparable to the Br$^-$ and I$^-$ structures discussed previously.

Figures 8A, 8B, 8C:
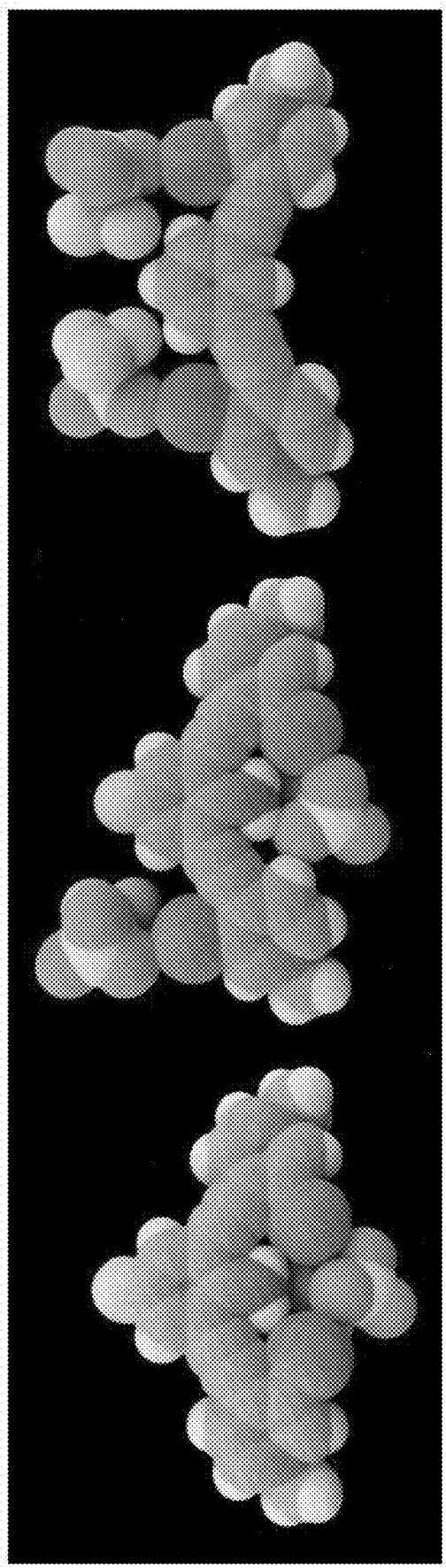
FIG. 8 shows 3D prints generated from the crystal structures (vdW radii) of disordered G2XBme$^{2+}$•2OTf in the bidentate (a) and S conformations (b) and G1XBme$^{2+}$•2OTf in the W conformation (c).

The crystal of G1XBme$^{2+}$•2OTf$^-$—lacking the preorganizing amine—adopts the W conformation (FIG. 8c). Crystallographic symmetry of this structure dictates a single unique XB contact with a distance and angle of 2.886(3) Å and 169.28(10)° ($R_{IO}$ value of 0.82). This contact is shorter than those observed in G2XBme$^{2+}$•2OTf$^-$, likely a result of each OTf$^-$ anion accepting only one XB. Unfortunately, the structural differences prevent a direct comparison of XB strength between G2XBme$^{2+}$•2OTf$^-$ and G1XBme$^{2+}$•2OTf$^-$.

The crystals of G2XBme$^{2+}$ and G2XB$^{2+}$ confirm that intramolecular HB-XBs can preorganize a receptor while simultaneously enhancing the XB. The Br$^-$ and I$^-$ comlexes show a marked reduction in XB distance, signifying an increase in XB strength. Furthermore, G2XBme$^{2+}$ and G2XB$^{2+}$ are more planar due to intramolecular HB-XB preorganization. The amine limits the monodentate conformation observed in G2XBme$^{2+}$•2OTf$^-$, which further supports preorganization. These crystallographic studies demonstrate the dual function of the intramolecular HB-XB to simultaneously preorganize and strengthen the XB.

EXAMPLE B

A pair of 2,6-bis(4-ethynylpyridinyl)-4-fluoroaniline receptors (2a and 2b). Solution studies, crystal structures and computations supported our hypothesis that the intramolecular HB between the electron-deficient aniline and the two XB donor iodine atoms enhance the electrophilicity of the XB donors and preorganizes the bidentate XBing conformation. We refer to this new preorganization strategy as intramolecular HB-XB. Receptor 2b, lacks XB donors and was prepared to quantify C—H HBing and serve as a control. While synthesizing and characterizing the receptors, solvent dependent color changes were observed, especially under ultraviolet light. To better understand this solvatochromism, UV-Visible absorption and fluorescence emission studies were conducted for 1a, 1b and octyl derivatives 2a and 2b.

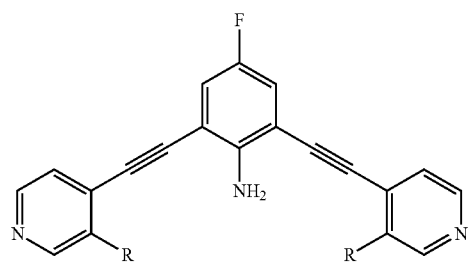

1a: R = I
1b: R = H

-continued

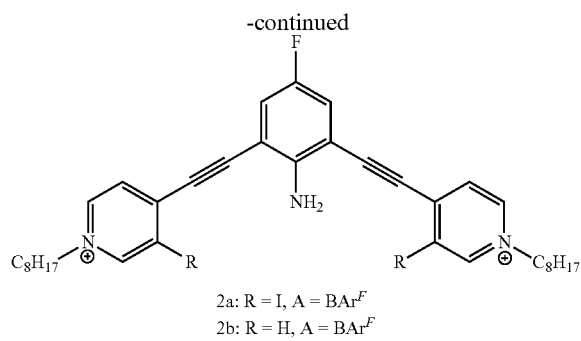

2a: R = I, A = BAr$^F$
2b: R = H, A = BAr$^F$

Figure 9:
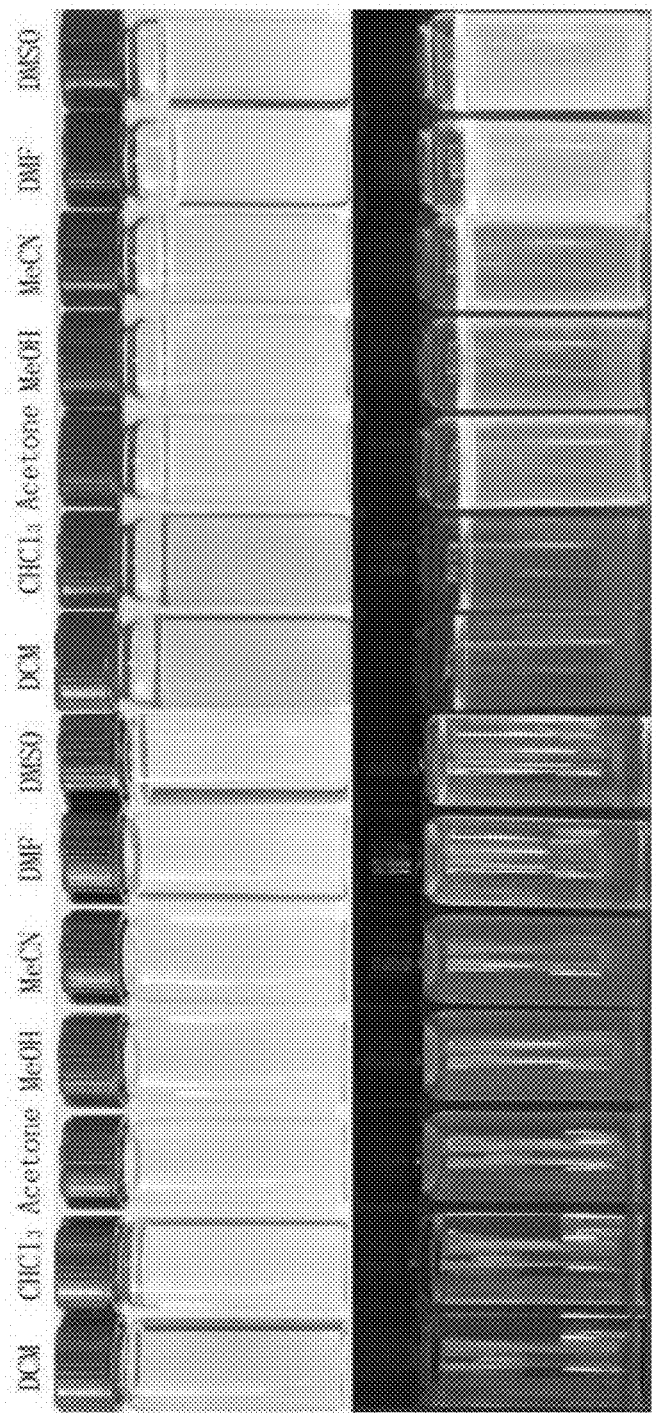
FIG. 9 demonstrates solvatochromism of 1 mM 1a (top left: under sunlight; bottom left: under 365 nm UV light) and 1b (top right: under sunlight; bottom right: under 365 nm UV light) in a set of solvents.

Solvent dependence of both the absorption and emission spectra was observed for 1a and 1b (FIG. 9). Receptors 1a and 1b exhibited a major absorbance band in the range of 300-600 nm. The absorption band of 1a is red shifted from 405 nm to 416 nm as the dielectric constant of the solvent is increased with the exception of MeCN. A similar roughly linear correlation of bathochromic shift with increasing solvent dielectric constant was obtained for 1b. Soret bands from π-π* transitions exhibit significant charge-transfer character resulting from the electron-deficient pyridine and electron donating aniline Other solvent parameters (dipole moment, E$_T$(30) and π* scale) were also analysed for both the neutral and charged receptors. However, no clear correlation between dipole moment, E$_T$(30) or π* scale and absorbance v$_{max}$ was observed suggesting that nonspecific solvent polarity effects are not strong determinants of the HOMO and LUMO energy levels. This lack of correlation and solvents that deviate from the trend may be due to the Lewis acidic nature of the studied receptors. Taken together, these results suggest that the dielectric constant of the solvent most influences the HOMO and LUMO energy levels of the receptors. High dielectric solvents stabilize the excited state more than the ground state of the receptor. As a result, the energy for the HOMO to LUMO electron transition is lowered producing a bathochromic shift of the spectra with increasing solvent dielectric constant. The λ$_{max}$ of 1a is always red shifted when compared to 1b in the same solvent, a result of the auxochrome iodine groups in 1a.

Figure 10:
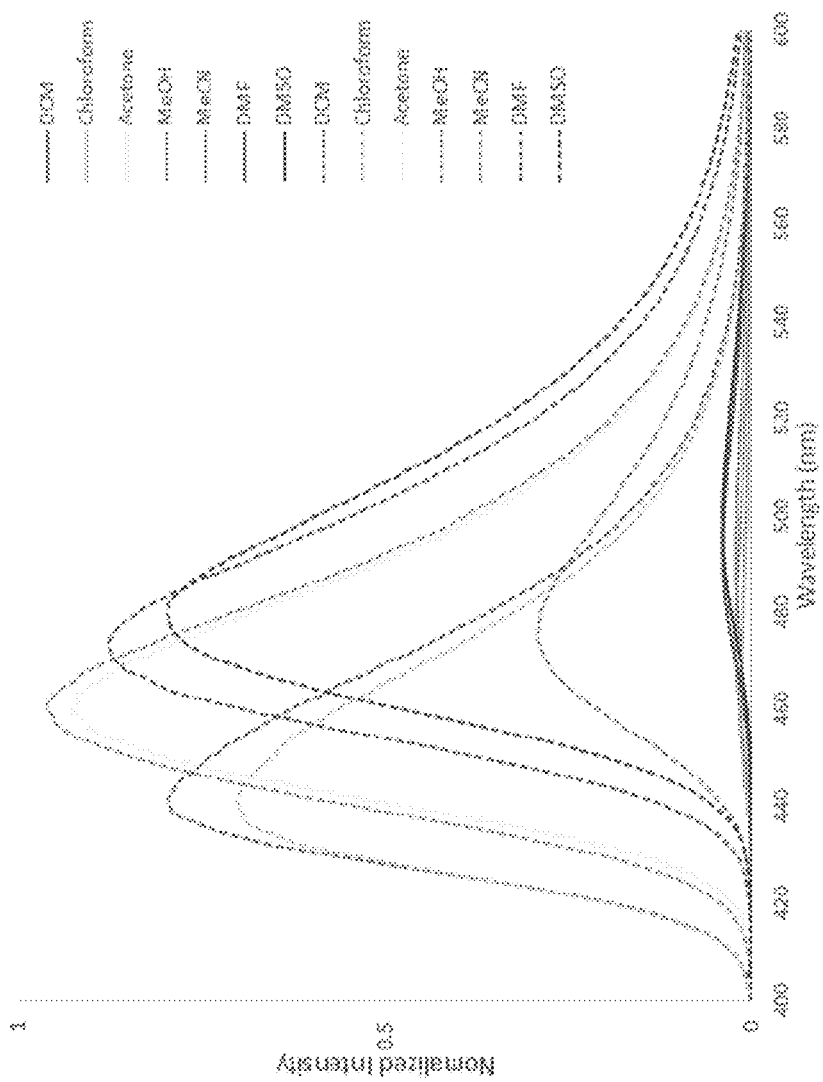
FIG. 10 is normalized fluorescence emission spectra of 1a (20 μM, solid line) and 1b (20 μM, dashed line) in various solvents.

The solvatochromic effect on fluorescence was also investigated for 1a and 1b. The iodine atoms of 1a produce a "heavy atom effect" that enhances the probability of intersystem crossing leading to reduced fluorescence of 1a compared to 1b (FIG. 10). The emission spectra of 1a and 1b obey the same direct correlation between solvent polarity and λ$_{max}$ shift. However, methanol deviates from this trend for both 1a and 1b. For instance, the emission band of 1b in methanol has a λ$_{max}$ at 475 nm which is 15 nm and 14 nm longer than in acetone and acetonitrile, respectively, and is even close to dimethylformamide (DMF, λ$_{max}$=476 nm). This deviation could result from the HB ability of the protic methanol. HBing to the amine of the fluoroaniline through an NH•••O type HB or to a pyridine nitrogen through an OH•••N HB could stabilize the excited state and shift the emission. Additionally, a drop in emission is observed for 1b, perhaps due to HB enhanced internal conversion and intersystem crossing.

To investigate the XB interaction and how it influences solvatochromism and fluorescence, the receptors were alkylated to increase their electron-deficiency and their binding affinity for anionic guests. Alkylation of the pyridines with octyl chains activated the XB and HB donors of 2a and 2b, respectively, while also enabling solubility in organic solvents.

Figures 11A, 11B, 11C, 11D:
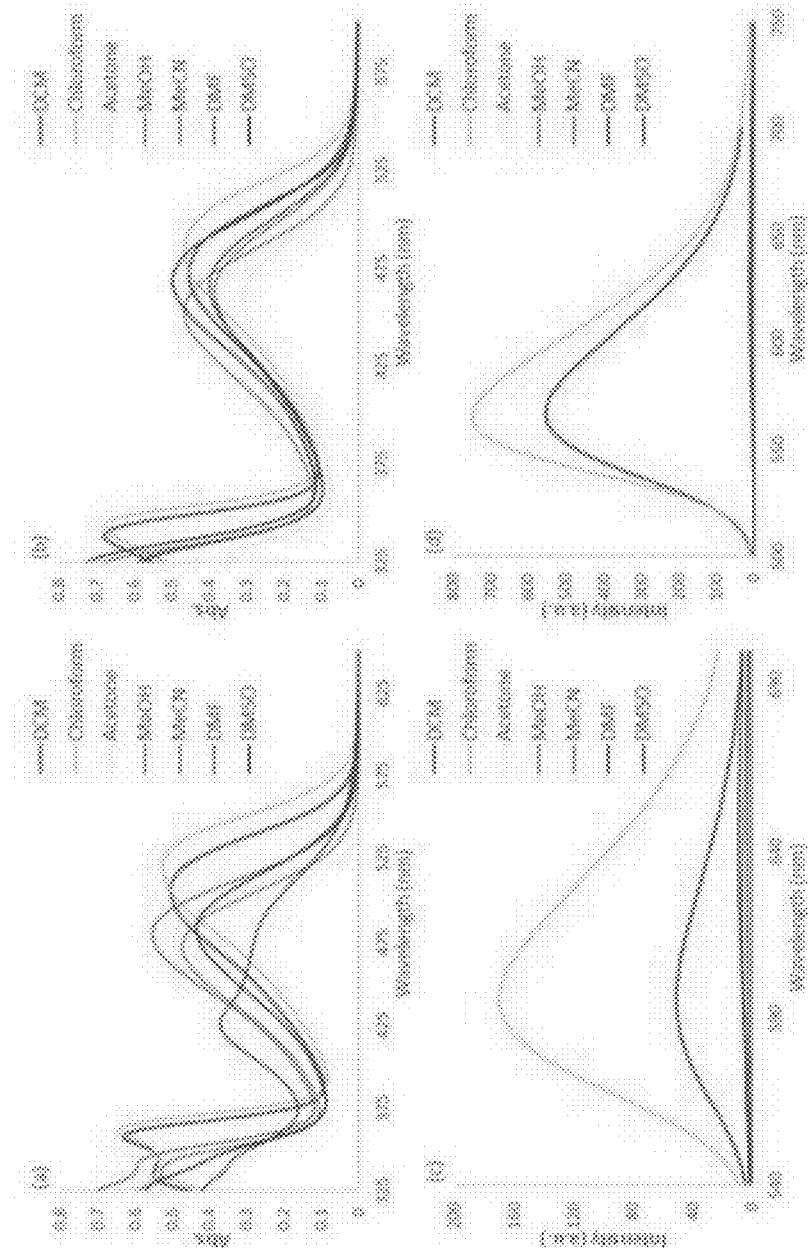
FIG. 11 is absorption spectra of 2a (a) and 2b (b) in various solvents. Fluorescence emission spectra of 2a (c)

The UV-Vis absorption and fluorescence emission spectra of 2a and 2b in various solvents are reported in FIG. 11. A negative solvatochromism was observed in DCM, acetone, MeCN and DMF for the absorption of both 2a and 2b which has also been observed in other pyridinium systems. This phenomenon has been explained by the ground state being more polar than the excited state and intramolecular charge transfer being favored by polar solvents. This produces a larger energy difference between the ground and excited states as the polarity of the solvent increases. Chloroform, MeOH and DMSO deviate from this trend, perhaps, due to the binding between the receptors and solvents or environment effect which give rise to conformational changes in the receptor molecule. Additionally, an obvious difference between 2a and 2b is the large blue shifting of 2a in DMF. A linear free energy relationship between the absorbance (v$_{max}$) of 2a and 2b showed that the absorbance of 2a is shifted more in DMF compared to 2b. We have solution and crystallographic evidence that derivatives of 2a can XB to the DMF carbonyl oxygen. This binding interaction may further stabilize the ground state. Ultimately, an 80 nm blue shift of absorbance in DMF is observed compared to DCM (FIG. 11a). The HB in 2b has a similar but weaker effect, shifting the absorption peak from 472 nm in DCM to 466 nm in DMF (FIG. 11b).

2a was only fluorescent in nonpolar solvents (DCM and chloroform) and was nearly quenched in all other solvents (FIG. 11c). In contrast, 2b had stronger fluorescence than 2a due to lack of the heavy atom effect, but was also quenched in polar solvents (FIG. 11d). The fluorescence quenching is consistent with other probes that are weakly fluorescent in hydrophilic environments but strongly fluorescent in hydrophobic environments.

Figure 12:
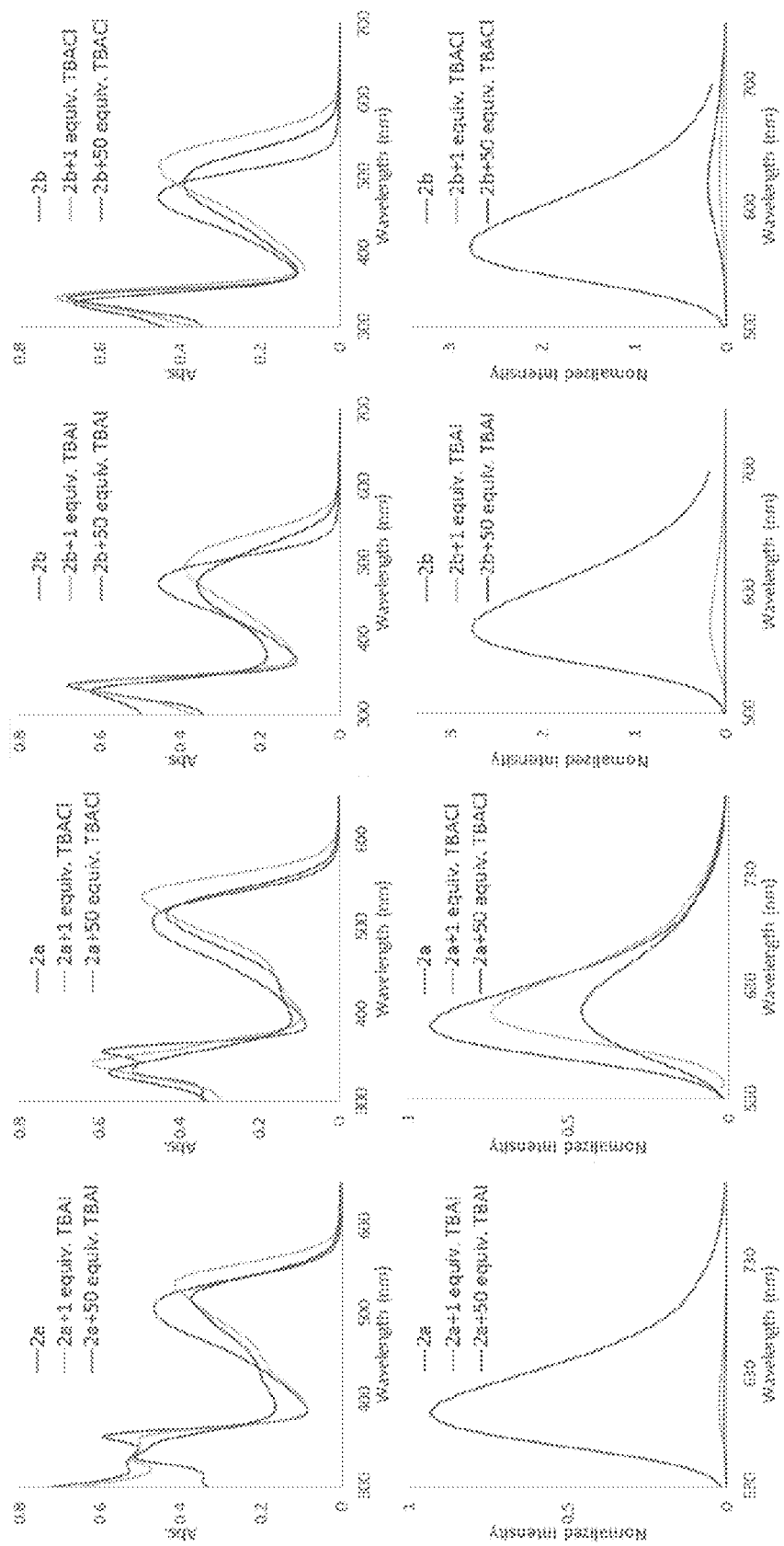
FIG. 12 is absorption spectra of 2a with $TBA^+I^-$ (top left) and with $TBA^+Cl^-$ (top middle-left), 2b with $TBA^+I^-$ (top middle-right) and with $TBA^+Cl^-$ (top right); followed by fluorescence emission spectra of 2a with $TBA^+I^-$ (bottom left) and with $TBA^+Cl^-$ (bottom middle-left), 2b with $TBA^+I^-$ (bottom middle-right) and with $TBA^+Cl^-$ (bottom right). All spectra were recorded at 20 μM of receptor in DCM solution (for excitation wavelengths and details see SI).
Figure 13:
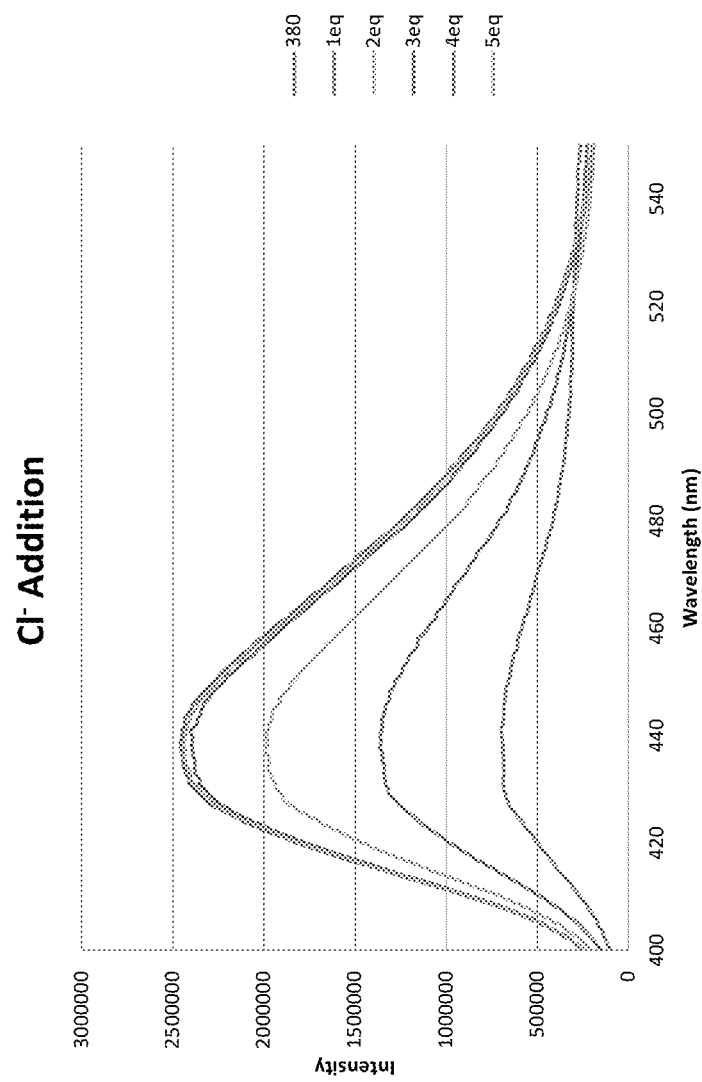
FIG. 13 shows fluorescence data for an illustrative compound. A 30 μM solution of a sulfone receptor compound with $PF_6^-$ counterion in wet DMSO was prepared and fluorescence spectra was obtained at excitation wavelength 300 nm which resulted in a weak fluorescent signal at 437 nm. Into the cuvette was titrated additions of tetrabutylammonium chloride. The intensity of the fluorescence signal increased with each subsequent addition up to 3 equivalence of anion added.
Figure 14:
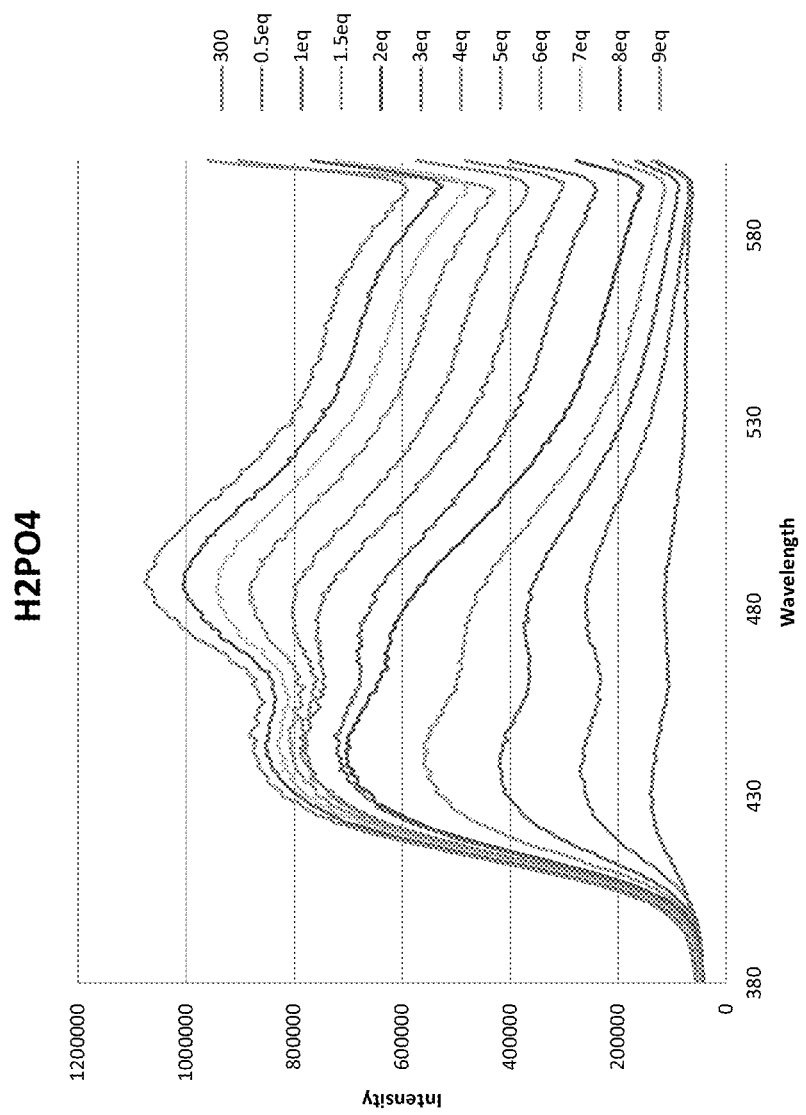
FIG. 14 shows fluorescence data for an illustrative compound. A 30 μM solution of a $CF_3$ receptor compound with $PF_6^-$ counterion in wet DMSO was prepared and fluorescence spectra was obtained at excitation wavelength 300 nm which resulted in two weak fluorescent signals at 441 nm and 483 nm. Into the cuvette was titrated additions of tetrabutylammonium hydrogen phosphate. The intensity of the fluorescence signal increased with each subsequent addition reaching a saturation at around 4 equivalence for the peak at 441 nm with marginal increased intensity out to 9 equivalence added.

Qualitative evaluation of the anion sensing capability of 2a and 2b in DCM was performed with a series of anions as their tetrabutylammonium salts (Cl$^-$, Br$^-$, I$^-$, SCN$^-$, NO$_3^-$, HSO$_4$, H$_2$PO$_4$ and ReO$_4$). Considering both solubility and polarity which may affect the noncovalent interaction between receptor and anion, we chose DCM as the solvent for these studies. The results are illustrated in FIG. 12. In general, the absorption band of XB receptor 2a at λ$_{max}$ 507 nm is red shifted from 509 to 535 nm when one molar equivalent of anion is added, and hypochromically blue shifted after the addition of excess anion (50 molar equivalents). Additionally, the absorption band of HB receptor 2b at 472 nm behaves similarly to 2a which is red shifted from 479 to 513 nm in the presence of one equivalent of anion and hypochromically blue shifted upon addition of excess anion (50 molar equivalents).

In the emission spectra, halides quenched the fluorescence of both 2a and 2b from 0 equivalent to 50 equivalents. For instance, fluorescence of 2a decreased by 20% after adding one equivalent of TBA$^+$Cl$^-$ and declined to 50% of the initial value after 50 equivalents (FIG. 12, bottom middle-left). However, the receptor is more sensitive to iodide (FIG. 12, bottom left). The intensity significantly dropped to 2% of the original level at just one equivalent of iodide. Inter and intramolecular HBing have been shown to facilitate fluorescence quenching. The efficient fluorescence "turn-off" in 2a correlates with previous NMR studies that illustrate stronger binding between 2a and I$^-$ compared to other halide anions. Specifically, the K$_{11}$ values determined by titrations of 2a with I$^-$, Br$^-$ and Cl$^-$ were 36,869 M$^{-1}$, 34,145 M$^{-1}$ and 23,622 M$^{-1}$ respectively in 40% CDCl$_3$/60% CD$_3$NO$_2$. In the current system, the formation of strong XBs (C—I•••I$^-$) in the 2a-I$^-$ complex could allow the necessary spin-orbital coupling for fluorescence quenching to occur. Moreover, the iodine and iodide present can act as heavy-atom quenchers. Considering these effects, intersystem crossing could be favored which leads to fluorescence quenching. Compared to 2a, fluorescence quenching of 2b is more efficient with chloride and bromide, and similar with iodide. These results could partially be explained by the weaker binding ability of 2b ($K_{11}$ for $I^-$, $Br^-$ and $Cl^-$ are 1,820 $M^{-1}$, 2,122 $M^{-1}$ and 2,326 $M^{-1}$, respectively in 40% $CDCl_3$/60% $CD_3NO_2$). In addition, thiocyanate ($SCN^-$) quenched the fluorescence of both 2a and 2b. $SCN^-$ decreased fluorescence intensity of 2a to less than 35% of the original level at one equivalent but changed very little at 50 equivalents. However, the fluorescence of 2b was almost totally quenched after 50 equivalents.

Some of the oxoanions studied elicited different fluorescence responses compared to halides and $SCN^-$. $NO_3^-$ and $ReO_4^-$ induced a similar fluorescence response in 2a and 2b as $SCN^-$ did. However, $H_2PO_4^-$ produced a 51% and 60% decrease in 2a and 2b, respectively, at one equivalent and totally quenched fluorescence when in excess. $HSO_4^-$ affected the fluorescence of 2b in a similar way to SCN, $NO_3$ and $ReO_4$. However, in 2a, the solution turned cloudy and floccule formed, precipitating out the receptor in a couple minutes upon the addition of 50 equivalents of $HSO_4^-$. In general, 2b is quenched more than 2a with all anions, except for iodide. One hypothesis is that XB between 2a and the anions rigidifies the structure of the 2a anion complex. The more planar/rigid structure which has less vibrational modes to absorb the excess energy leads to less efficient internal conversion. Thus, the more efficient internal conversion of 2b causes the lower quantum yield, and correspondingly lower fluorescence intensity.

Geometry optimizations and Frontier molecular orbital calculations were performed to further analyse the spectrophotometric properties of the receptors. Density Functional Theory (DFT) calculations were done using the B3LYP/6-31+G(d,p) functional. To simplify calculations, methyl derivatives of the charged receptors were evaluated. The neutral receptors 1a and 1b have nearly equivalent HOMO and LUMO distributions. Additionally, 2a and 2b also have analogous HOMO and LUMO maps which is consistent with the similarly shaped absorption and emission spectra. The electron density in the HOMO is mainly populated on the central fluoroaniline ring. In the LUMO the electron density is increased on the two flanking pyridine rings. Such electronic configurations lead to the charge-transfer nature of the electronic transitions. Narrower energy band gaps are predicted for the HOMO and LUMO for the halogen containing receptors (1a and 2a) compared to the HB receptors (1b and 2b) which correlate with the larger $\lambda_{max}$ (for both the absorption and emission) observed for the halogen containing receptors 1a and 2a.

In summary, we have demonstrated that XB receptor 1a and HB receptor 1b exhibited similar solvatochromism in their UV-Vis and fluorescence spectra. As compared to 1a and 1b, octyl derivatives 2a and 2b exhibited opposite solvatochromism corresponding to their charged states and differences in binding ability. Theoretical estimations of the electron density distributions of the HOMOs and LUMOs highlighted the charge transfer nature of the receptors and supported the differences observed in the soret band $\lambda_{max}$ in the UV-Vis spectra. The anion induced fluorescence quenching of XB derivative 2a is less efficient than 2b with most anions, possibly due to the loose bolt effect for the weaker binding 2b. Additionally, 2a can selectively sense $I^-$ over other anions by a significant fluorescence quenching after the addition of one equivalent.

In view of the many possible embodiments to which the principles of the disclosed invention may be applied, it should be recognized that the illustrated embodiments are only preferred examples of the invention and should not be taken as limiting the scope of the invention.

What is claimed is:
1. A compound, or a protonate or salt thereof, of formula I:

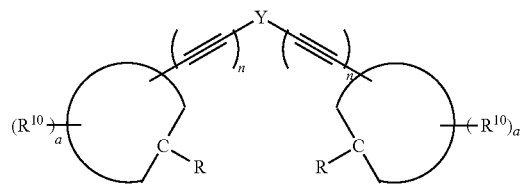

Formula I wherein Y is

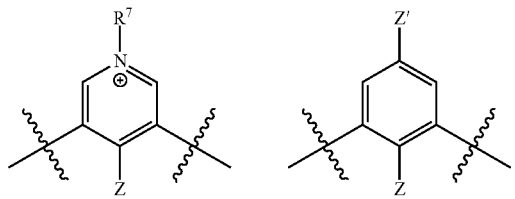

wherein Z is hydrogen, halogen, amino, substituted amino, hydroxy, amido, urea or sulfonamido; and $R^7$ is hydrogen, alkyl, substituted alkyl, or polyethylene glycol;
n is 1 or 2;
each $R^{10}$ is independently ethyl, n-propyl, isopropyl, n-butyl, isobutyl, t-butyl, pentyl, hexyl, heptyl, octyl, decyl, tetradecyl, hexadecyl, eicosyl, tetracosyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;
a is 1 to 4;

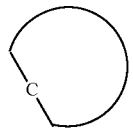

is an aryl or heteroaryl ring; and
each R is independently halogen, carbonylamino, sulfonamide, carboxylic acid or hydrogen, provided at least one R is a halogen.
2. The compound of claim 1, wherein
$R^7$ is $C_1$-$C_6$ alkyl, alkoxyalkyl, aminoalkyl or sulfonylalkyl.
3. The compound of claim 2, wherein $R^7$ is methyl.
4. The compound of claim 1, wherein Z is —$NH_2$, —Br, or —I.
5. The compound of claim 1, wherein n is 1.
6. The compound of claim 1, wherein a is 1.

7. The compound of claim 1, wherein the

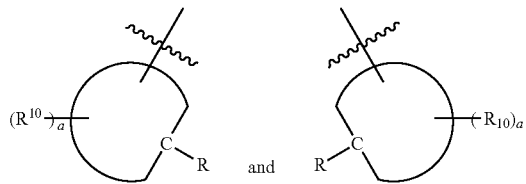

portions of the compound of formula I are:

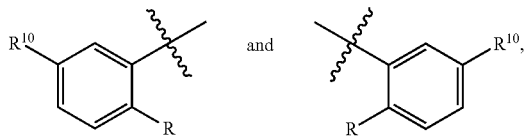

respectively, or

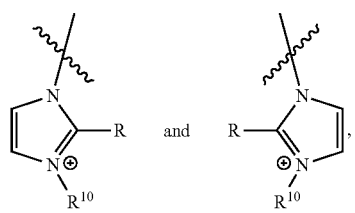

respectively, or

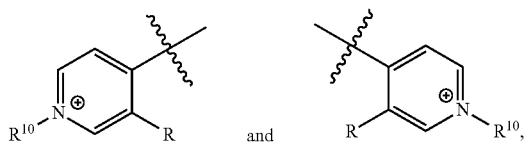

respectively.

8. The compound of claim 1, wherein $R^{10}$ is substituted alkyl, substituted sulfonyl, or substituted carboxyl.

9. The compound of claim 1, wherein $R^{10}$ is —$CF_3$, sulfonyl$C_{1-6}$alkyl, or —COOR wherein R is alkyl.

10. The compound of claim 1, wherein a is 1 and both $R^{10}$ are the same.

11. The compound of claim 1, wherein at least one R is —I.

12. The compound of claim 1, wherein both R groups are —I.

13. The compound of claim 1, wherein the compound is protonated.

14. The compound of claim 1, wherein the

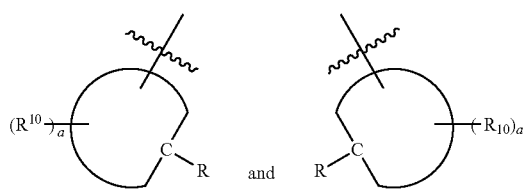

portions of the compound of formula I are:

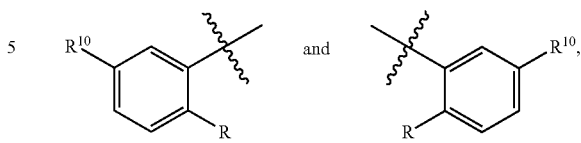

respectively.

15. The compound of claim 14, wherein both R groups are —I.

16. A receptor-ligand structure comprising the compound of claim 1 as a receptor and a ligand.

17. A receptor-ligand structure comprising the compound of claim 1 as a receptor and a ligand that includes at least one anion selected from $Cl^-$, $Br^-$, $I^-$, $H_2PO_4^-$, $HSO_4^-$, $ClO_4^-$, $NO_3^-$, $PF_6^-$, $TsO^-$, $OTf^-$, $BAr^{F-}$, $BF_4^-$, $HS^-$, $SbF_6^-$, $ReO_4^-$, $TcO_4^-$ or $SCN^-$.

18. A method for detecting for the presence of an anion in a system, comprising contacting a sample from the system with a compound, or a protonate or salt thereof, of claim 1.

19. A compound, or a protonate or salt thereof, of formula I:

Formula I

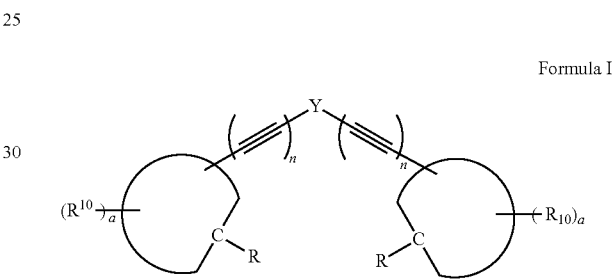

wherein Y is

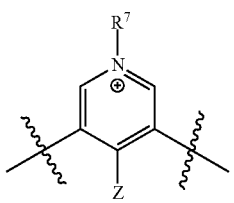

wherein $R^7$ is $C_1$-$C_6$ alkyl, alkoxyalkyl, aminoalkyl or sulfonylalkyl, and Z is halogen, amino, substituted amino, hydroxy, amido, urea or sulfonamido;

n is 1 or 2;

each $R^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;

a is 0 to 4;

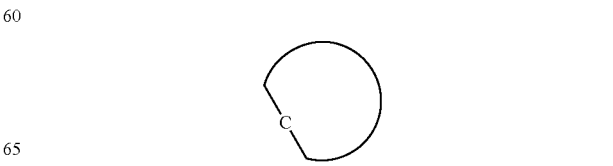

is an aryl or heteroaryl ring; and
each R is independently halogen, carbonylamino, sulfonamide, carboxylic acid or hydrogen, provided at least one R is a halogen.

20. The compound of claim 19, wherein a is 0.

21. The compound of claim 19, wherein at least one R is —I.

22. The compound of claim 19, wherein both R groups are —I.

23. The compound of claim 19, wherein Z is —NH$_2$, —Br, or —I.

24. The compound of claim 19, wherein Z is amino.

25. A compound, or a protonate or salt thereof, of formula I:

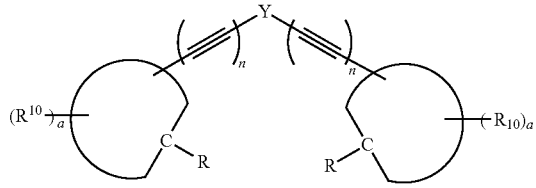

Formula I wherein Y is

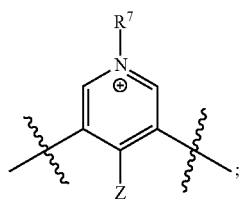

wherein Z is hydrogen, halogen, amino, substituted amino, hydroxy, amido, urea or sulfonamido; and R$^7$ is hydrogen, alkyl, substituted alkyl, or polyethylene glycol;
n is 1 or 2;
each R$^{10}$ is independently alkyl, substituted alkyl, a polyether moiety, carboxyl, substituted carboxyl, alkoxy, substituted alkoxy, haloalkyl, halogen, nitro, amino, aryloxy, aryl, substituted aryl, cyano, hydroxyl, carbonylamino, aminocarbonyl, acyl, sulfonyl, or substituted sulfonyl;
a is 0 to 4;

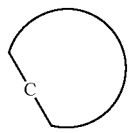

is an aryl or heteroaryl ring; and
each R is independently halogen, carbonylamino, sulfonamide, carboxylic acid or hydrogen, provided at least one R is —I; and
provided that if Y is

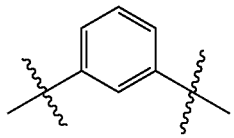 [SMILES: *c1cccc(*)c1]

then

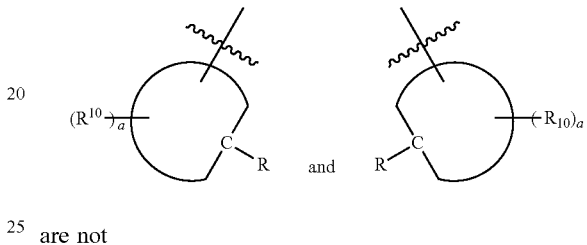

are not

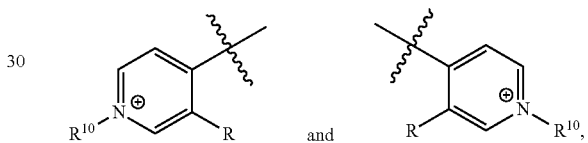

respectively.

26. The compound of claim 25, wherein the

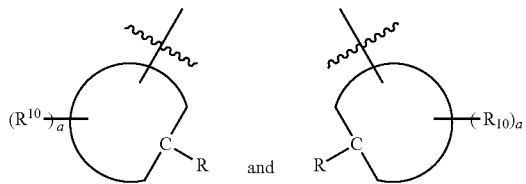

portions of the compound of formula I are:

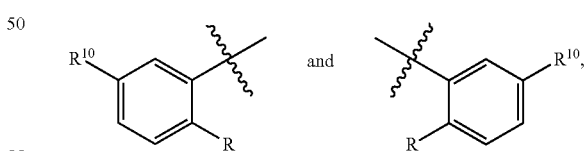

respectively.

27. The compound of claim 25, wherein both R groups are —I.

* * * * *